(12) United States Patent
Hlasta et al.

(10) Patent No.: US 7,259,263 B2
(45) Date of Patent: Aug. 21, 2007

(54) METHOD OF SYNTHESIS OF AZOLE-CONTAINING AMINO ACIDS

(75) Inventors: Dennis J. Hlasta, Doylestown, PA (US); Craig A. Zificsak, Harleysville, PA (US)

(73) Assignee: Jansen Pharmaceutica N.V. (BE)

( * ) Notice: Subject to any disclaimer, the term of this patent is extended or adjusted under 35 U.S.C. 154(b) by 81 days.

(21) Appl. No.: 11/170,042

(22) Filed: Jun. 29, 2005

(65) Prior Publication Data

US 2007/0004728 A1      Jan. 4, 2007

(51) Int. Cl.
C07D 223/64    (2006.01)
C07D 263/24    (2006.01)
C07D 413/06    (2006.01)
C07D 471/02    (2006.01)

(52) U.S. Cl. .................. 548/311.1; 548/339.1; 548/232; 548/229; 546/121

(58) Field of Classification Search .......... 548/203, 548/230, 311.1, 339.1, 232, 229; 546/121
See application file for complete search history.

(56) References Cited

OTHER PUBLICATIONS

Hecht et al. "Synthesis of L-erythro-beta-Hydroxyhistidine from D-Glucosamine". *J. American Chem. Soc.*, 1979, pp. 3982-3983 vol. 101. XP002371212.
Garner P. Stereocontrolled Addition To A Penaldic Acid Equivalent: An Asymmetric Synthesis of Threo-β-Hydroxy-L-Glutamic Acid. Tetrahedron Lett., 1984, pp. 5855-5858, vol. 25, No. 51.
Otsuka M. et al. "Synthetic study towards man-designed bleomycins. Synthesis of a DNA cleaving molecule based on bleomycin" *Tetrahedron Letters*. 1986, pp. 3639-3642, vol. 27, No. 31, XP002371210.
Kittaka A. et al. "Transition-metal binding site of bleomycin. A remarkably efficient dioxygen-activating molecule based on bleomycin-FE(II) complex". *Tetrahedron Letters*, 1986, pp. 3631-3634, vol. 27, No. 31, XP002371211.
Kittaka et al. "Synthetic models for the transition metal binding site of bleomycin. Remarkable Improvement of dioxygen activating capability". *Tetrahedron*, 1988, pp. 2811-2820, vol. 44, No. 10.
Lubell, W. et al., "Surrogates for Chiral Aminomalondialdehyde. Synthesis of N-(9-Phenylfluoren-9-yl) serinal and N-(9-Phenylfluoren-9-yl)vinylglycinal." *J. Org. Chem.*, 1989, pp. 2824-2831, vol. 54.
Dondoni A. et al., "Stereochemistry Associated with the Addition of 2-(Trimethylsilyl)thiazole to Differentially Protected α-Amino Aldehydes. Applications toward the Synthesis of Amino Sugars and Sphingosines." *J. Org. Chem.* 1990, pp. 1439-1446, vol. 55.

Saeed, A., "Synthesis of L-β-Hydroxyaminoacids Using Serine Hydroxymethyltransferase." *Tetrahedron*, 1992, pp. 2507-2514, vol. 48, No. 12.
Dondoni A. et al. "2-Thiazolyl-Amino Ketones: A new class of reactive intermediates for the stereocontrolled synthesis of unusual amino acids". *Synthesis*, 1993, pp. 1162-1176, vol. 11, XP002371216.
Dondoni A. et al. "Chelation-and Non-chelation-controlled addition of 2-(Trimethylsilyl)thiazole to alpha-Amino Aldehydes: Stereoselective synthesis of the beta-amino-alpha-hydroxy Aldehyde." Stereoselective Synthesis of the β-Amino-α-hydroxy Aldehyde Intermediate for the Preparation of the Human Immunodeficiency Virus Proteinase Inhibitor Ro 31-8959. *J. Org. Chem.*, 1995, pp. 8074-8080, vol. 60, No. 24, XP002371214.
Dondoni A. et al: "Total synthesis of (+)-Galactostatin. An Illustration of the utility of the thiazole-aldehyde synthesis". *J. Org. Chem.*, 1995, pp. 4749-4754, vol. 60, No. 15, XP002371215.
Kimura T., "Enzymatic Synthesis of β-Hydroxy-α-amino Acids Based on Recombinant D- and L-Threonine Aldolases." *J. Am. Chem. Soc.*, 1997, pp. 11734-11742, vol. 119.
Zhao, M. et al., "Oxidation of Primary Alcohols to Carboxylic Acids with Sodium Chlorite Catalyzed by TEMPO and Bleach." *J. Org. Chem.* 1999, pp. 2564-2566, vol. 64.
Liang, X. et al., "Garner's aldehyde" *Royal. Soc. Chem.*, 2001, pp. 2136-2157.
Palian, M.M. et al., "Lipo α-Amino-β-hydroxy Acids and O-Linked Glycosides: Building Blocks for Ceramyl and Glycosphingoyl Peptides." *J. Org. Chem.*, 2001, pp. 7178-7183, vol. 66.
Dong et al. "Total Synthesis of Exochelin MN and Analogues". *J. Org. Chem.*, 2002, pp. 4759-4770, vol. 67, No. 14, XP002371209.
Barma, D.K. et al., "Dimethylthiocarbamate (DMTC): An Alcohol Protecting Group.9" *Organic Letters*, 2003, pp. 4755-4757, vol. 25, No. 25.
PCT International Search Report dated Mar. 21, 2006 for PCT Application No. PCT/US2005/023048 which relates to U.S. Appl. No. 10/170,042.

*Primary Examiner*—Kamal A. Saeed
*Assistant Examiner*—Jason M. Nolan

(57) ABSTRACT

The invention relates to methods of synthesizing 2-substituted azole compunds of formula (I):

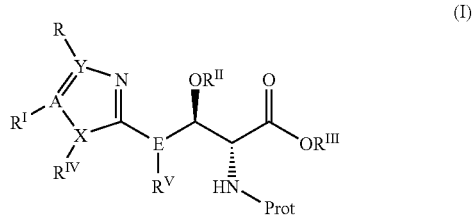

The invention is also relates to compounds of formula (I) and to intermediate compounds in the synthesis method.

56 Claims, No Drawings

METHOD OF SYNTHESIS OF AZOLE-CONTAINING AMINO ACIDS

CROSS-REFERENCE TO RELATED APPLICATIONS

Not applicable.

STATEMENT REGARDING FEDERALLY SPONSORED RESEARCH OR DEVELOPMENT

The research and development of the invention described below was not federally sponsored.

BACKGROUND OF THE INVENTION 1,3-Azole-containing amino acids have utility as analogues of natural amino acids for incorporation into biologically active molecules. In particular, they are constituent parts of many biologically active peptides and are useful in preparing antimicrobial agents. Currently, no general method for their synthesis exists.

Saeed and Young have described the synthesis of L-beta-hydroxy amino acids using an enzymatic method (Saeed, A; Young, D. W; *Tetr.* 1992, 48, 2507-2514). Their method does not produce the 1,3-azole-containing amino acids synthesized by the present inventive method, and their route gives a mixture of isomeric forms.

Kimura et al. report another enzymatic synthesis of beta-hydroxy-amino acids. (Kimura, T. et al., *J. Am. Chem. Soc.* 1997 119, 11734-11742). Their synthesis, however, provides mixed stereochemistry at the beta-carbon.

Dalla Croce et al. report a stereoselective aldol addition of a chiral glycine enolate synthon (Dalla Croce, P. et al., *Heterocycles,* 2000, 52, 1337-1344). Their method, however, produces only moderate yields and they do not report synthesis of any 1,3-azole-containing acids.

Palian and Polt report synthesis of lipophilic beta-hydroxy amino acids (Palian, M; Polt, R., *J. Org. Chem.,* 2001, 66, 7178-7183). These authors do not describe the methods of the present invention and they do not describe the synthesis of 1,3-azole-containing amino acids.

Zhao et al. reported oxidation of primary alcohols to carboxylic acids using TEMPO catalyst along with sodium chlorite and bleach (Zhao et al., *J. Org. Chem.,* 1999, 64, 2564-2566). They did not apply their method, however, to produce beta-hydroxy amino acids.

Barma et al. reported an oxidative removal of the N,N-dimethylthiocarbamate group from alcohols (Barma et al., *Org. Lett.,* 2003, 5, 4755-4757). These authors do not describe the synthesis of 1,3-azole-containing amino acids.

The Garner aldehydes (Garner, P. *Tetr. Lett.,* 1984, 25, 5855-5858; Liang, X, et al., *J. Chem. Soc. Perkin Trans. 1,* 2001, 2136-2157), for which both the S and R configurations are commercially available, are configurationally stable under many reaction conditions that are typically employed for the elaboration of the aldehyde functionality. Lubell and Rapoport introduced the phenylfluorenyl-protected oxazolidone as a serinal equivalent similar to Garner's aldehyde, and the inclusion of the phenylfluorenyl moiety greatly stabilizes the configuration of the α-proton in products under basic conditions (Lubell, W; Rapoport, H; *J. Org. Chem.,* 1989, 54, 3824-3831). It has seen only limited utility in organic synthesis and has been commented by Rapoport that the phenylfluorenyl group is known to be more acid-stable than the related trityl group for other substrates. Both of these substrates allow for the selective incorporation of nucleophiles into an intermediate for further derivatization.

Dondoni has utilized a variety of chiral, alpha-amino aldehydes as reactants in a condensation reaction with 2-trimethylsilylthiazole (Dondoni, A, et al., *J. Org. Chem.,* 1990, 55, 1439-1446). The use of Garner's aldehyde furnished the best results in terms of yield and selectivity. Dondoni and others have generally utilized this thiazole chemistry as a method to incorporate a formyl group, rather than functionalize the portion of the molecule derived from Garner's aldehyde.

Thus, there is a need for a generalized method to synthesize 1,3-azole-containing amino acids

SUMMARY OF THE INVENTION

The present invention is directed to a process for assembly of diverse, 2-substituted azole derivatives and novel intermediate compounds using available azoles as starting materials. The rapid synthesis of such highly complex drug-like molecules is unexpected and surprising.

Accordingly, the invention is directed to a method of synthesizing 2-substituted azole derivatives of formula (I):

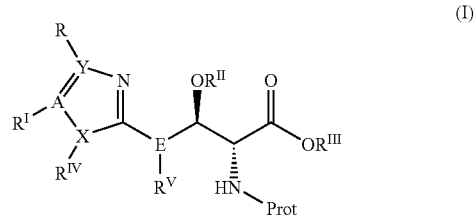

the method comprising
(a) reacting an aldehyde of formula (II)

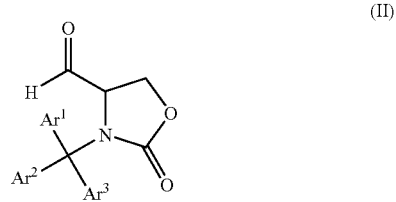

with an azole of formula (III)

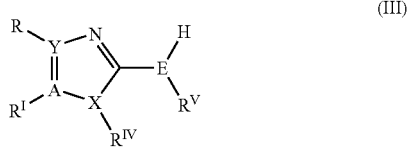

in the presence of a carbonylating agent of formula (IV)

to give an oxazolidone of formula (Ia)

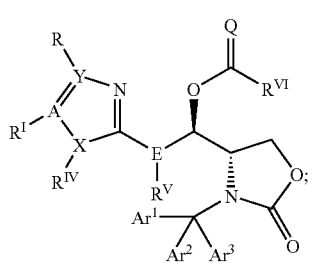

(Ia);

(b) reacting the the oxazolidone of formula (Ia) so as to hydrolyze the triarylmethyl group, cleave the O—(C=Q) bond, and open the oxazolidone, then reacting the resulting intermediate with Prot-Z wherein Prot-Z is an amino protecting agent selected from the group consisting of Prot-O-Prot, Prot-halide, Prot-N$_3$, R$^X$O$_2$C—OCO$_2$N=C(C$_6$H$_5$)CN, Prot-O-(1-benzotriazolyl), R$^X$O$_2$C—O—C$_6$F$_5$, R$^X$O$_2$C—O—C$_6$H$_4$—NO$_2$, R$^X$O$_2$C—O—CH(Cl)CCl$_3$, R$^X$O$_2$C—O-2-pyridyl, R$^X$O$_2$C—S-2-pyridyl, R$^X$O$_2$C—S—Ph, R$^X$O$_2$C—OSu, R$^X$O$_2$C-(1-imidazoyl), R$^X$O$_2$C—CN, R$^X$CO—O—C$_6$F$_5$, R$^X$CO—CN, Fmoc-Cl, Fmoc-N$_3$, Fmoc-O-(1-benzotriazolyl), Fmoc-OSu, or Fmoc-O—C$_6$F$_5$, to give an azole-containing intermediate of formula (Ib)

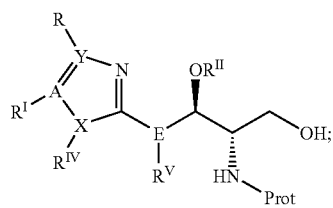

(Ib);

and (c) oxidizing the intermediate of formula (Ib) to give the 2-substituted azole derivative of formula (I);

An alternative method comprises (a) reacting an aldehyde of formula (II)

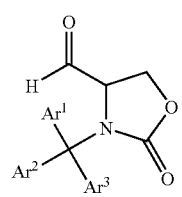

(II)

with an azole of formula (III)

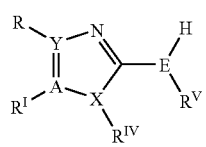

(III)

in the presence of a carbonylating agent of formula (IV)

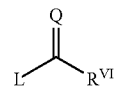

(IV)

wherein Q=S and R$^{VI}$ is —NR$^{VII}$R$^{VIII}$, to give an oxazolidone of formula (Ia)

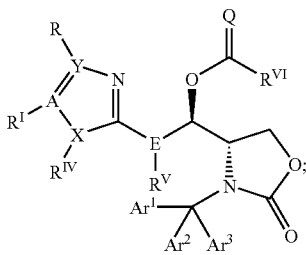

(Ia);

(b) reacting the oxazolidone of formula (Ia) so as to hydrolyze the triarylmethyl group, then reacting the resulting intermediate with Prot-Z wherein Prot-Z is an amino protecting agent selected from the group consisting of Prot-O-Prot, Prot-halide, Prot-N$_3$, R$^X$O$_2$C—OCO$_2$N=C(C$_6$H$_5$)CN, Prot-O-(1-benzotriazolyl), R$^X$O$_2$C—O—C$_6$F$_5$, R$^X$O$_2$C—O—C$_6$H$_4$—NO$_2$, R$^X$O$_2$C—O—CH(Cl)CCl$_3$, R$^X$O$_2$C—O-2-pyridyl, R$^X$O$_2$C—S-2-pyridyl, R$^X$O$_2$C—S—Ph, R$^X$O$_2$C—OSu, R$^X$O$_2$C-(1-imidazoyl), R$^X$O$_2$C—CN, R$^X$CO—O—C$_6$F$_5$, R$^X$CO—CN, Fmoc-Cl, Fmoc-N$_3$, Fmoc-O-(1-benzotriazolyl), Fmoc-OSu, or Fmoc-O—C$_6$F$_5$, to give an azole-containing intermediate of formula (Ic)

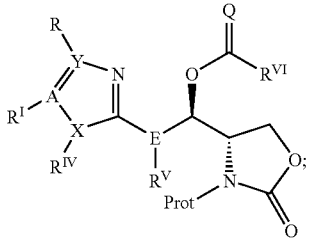

(Ic);

and (c) reacting the intermediate of formula (Ic), so as to hydrolyze the O—(C=Q) bond and oxazolidone then oxidize-the-intermediate to give the 2-substituted azole of formula (I).

Another alternative method comprises (a) reacting an aldehyde of formula (II)

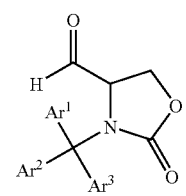

(II)

with an azole of formula (III)

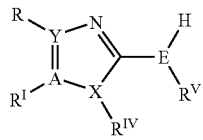
(III)

in the presence of a carbonylating agent of formula (IV)

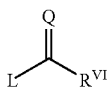
(IV)

to give an oxazolidone of formula (Ia)

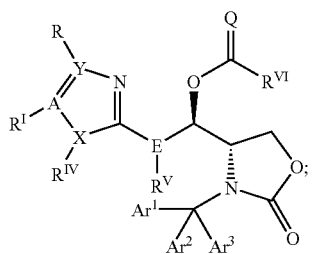
(Ia);

(b) reacting the oxazolidone of formula (Ia) so as to hydrolyze the triarylmethyl group, then reacting the resulting intermediate with Prot-Z wherein Prot-Z is an amino protecting agent selected from the group consisting of Prot-O-Prot, Prot-halide, Prot-N$_3$, R$^X$O$_2$C—OCO$_2$N=C(C$_6$H$_5$)CN, Prot-O-(1-benzotriazolyl), R$^X$O$_2$C—O—C$_6$F$_5$, R$^X$O$_2$C—O—C$_6$H$_4$—NO$_2$, R$^X$O$_2$C—O—CH(Cl)CCl$_3$, R$^X$O$_2$C—O-2-pyridyl, R$^X$O$_2$C—S-2-pyridyl, R$^X$O$_2$C—S—Ph, R$^X$O$_2$C—OSu, R$^X$O$_2$C-(1-imidazoyl), R$^X$O$_2$C—CN, R$^X$CO—O—C$_6$F$_5$, R$^X$CO—CN, Fmoc-Cl, Fmoc-N$_3$, Fmoc-O-(1-benzotriazolyl), Fmoc-OSu, or Fmoc-O—C$_6$F$_5$, to give an azole-containing intermediate of formula (Ic)

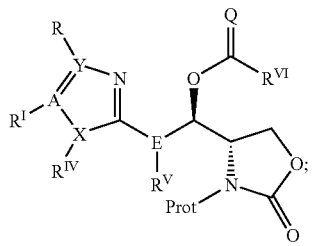
(Ic);

(c) reacting the intermediate of formula (Ic) so as to hydrolyze the O—(C=Q) bond, then reacting the intermediate with R$^{II}$-L to give an intermediate of formula (Id);

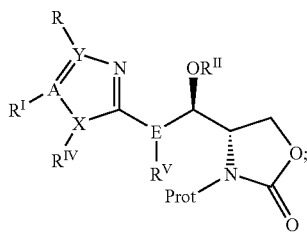
(Id);

and (d) reacting the intermediate of formula (Id) so as to hydrolyze the oxazolidone group, then oxidizing the intermediate to give the 2-substituted azole of formula (I);

In the above methods, unless otherwise specified,

Ar$^1$, Ar$^2$ and Ar$^3$ independently are phenyl or phenyl optionally substituted with halogen, C$_{1-8}$alkyl, C$_{1-8}$alkyloxy, nitro, C$_{1-8}$alkylamino, nitrile, or benzoyloxy;

X is N or S;

Y and A independently are C or N;

E is a direct bond or CH;

R and R$^I$ independently are H, C$_{1-8}$heteroalkyl, C$_{1-8}$alkyl, C$_{5-10}$aryl, heteroaryl, C$_{5-10}$arylC$_{1-8}$alkanyl, fluorinated C$_{1-8}$alkyl, heteroarylC$_{1-8}$alkanyl, halogen, nitrile, —NR$^{VII}$R$^{VIII}$, —OR$^{VII}$, —COR$^{VII}$—COOR$^{VII}$—CONR$^{VII}$R$^{VIII}$ or taken together form a five to eight membered carbocyclic or heterocyclic saturated or unsaturated ring, wherein the heteroaryl in any heteroaryl-containing R or R$^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

R$^{II}$ and R$^{III}$ independently are H, C$_{1-8}$heteroalkyl, C$_{1-8}$alkyl, C$_{5-10}$arylC$_{1-8}$alkanyl or C$_{1-8}$heteroalkyl;

R$^{IV}$ is H, C$_{1-8}$alkyl, C$_{5-10}$aryl, heteroaryl, C$_{5-10}$arylC$_{1-8}$alkanyl, C$_{1-8}$heteroalkyl, or taken together with R$^V$ forms a five to eight membered cyclic alkanyl or cyclic heteroalkanyl, wherein the heteroaryl in any heteroaryl-containing R$^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

R$^V$ is absent when E is a direct bond, H, C$_{1-8}$alkyl, C$_{5-10}$aryl, C$_{5-10}$arylC$_{1-8}$alkanyl, heteroaryl, or taken together with E and R$^{IV}$ forms a five to eight membered cyclic alkyl or cyclic heteroalkyl, wherein the heteroaryl in any heteroaryl-containing R$^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

R$^{VI}$ is C$_{1-8}$alkanyloxy or —NR$^{VII}$R$^{VIII}$;

R$^{VII}$ and R$^{VIII}$ independently are C$_{1-8}$alkyl, C$_{5-10}$aryl, C$_{5-10}$arylC$_{1-8}$alkanyl or taken taken together form a three to seven membered cyclic alkanyl or cyclic heteroalkanyl;

Q is O or S;

L is Cl, Br, I, F, OSO$_2$R$^{IX}$, O(CO)R$^{IX}$ or OCO$_2$R$^{IX}$;

R$^{IX}$ is fluorinated C$_{1-8}$alkyl, C$_{1-8}$alkyl C$_{5-10}$aryl, C$_{5-10}$aryl C$_{1-8}$alkanyl, or C$_{5-10}$heteroaryl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

The invention is also directed to compounds of formulas (I), (Ia), (Ib), (Ic), (Id), and (II) and to pharmaceutical compositions containing them.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Fluorinated alkyl" refers to a saturated branched or straight chain hydrocarbon radical derived by removal of 1 hydrogen atom from the parent alkane; the parent alkane contains from 1 to 6 carbon atoms with 1 or more hydrogen atoms substituted with fluorine atoms up to and including substitution of all hydrogen atoms with fluorine. Preferred fluorinated alkyls include trifluoromethyl substituted alkyls and perfluorinated alkyls; more preferred fluorinated alkyls include trifluoromethyl, perfluoroethyl, 2,2,2-trifluoroethyl, perfluoropropyl, 3,3,3-trifluoroprop-1-yl, 3,3,3-trifluoroprop-2-yl, 1,1,1,3,3,3-hexafluoroprop-2-yl; a particularly preferred fluorinated alkyl is trifluoromethyl.

"Fluorinated alkanyloxy" refers to a radical derived from a fluorinated alkyl radical attached to an oxygen atom with the oxygen atom having one open valence for attachment to a parent structure.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_{1-8}$) alkyl, with ($C_{1-3}$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl:" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is ($C_{2-8}$) alkenyl, with ($C_{2-3}$) being particularly preferred.

"Alkynyl:" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is ($C_{2-8}$) alkynyl, with ($C_{2-3}$) being particularly preferred.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is ($C_{1-8}$) alkyldiyl, with ($C_{1-8}$) being particularly preferred. Also preferred are saturated acyclic alkandiyl radicals in which the radical centers are at the terminal carbons, e.g., methandiyl; ethan-1,2-diyl; propan-1,3-diyl; butan-1,4-diyl; and the like (also referred to as alkylenos, as defined infra).

"Vic Alkyldiyl:" refers to a saturated or unsaturated, branched, straight-chain or cyclic hydrocarbon radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2-diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is $(C_{2-8})$ vic alkyldiyl, with $(C_{2-3})$ being particularly preferred.

"Gem Alkyldiyl:" refers to a saturated or unsaturated, branched, straight-chain or cyclic hydrocarbon radical having one divalent radical center derived by the removal of two hydrogen atoms from a single carbon atom of a parent alkane, alkene or alkyne. The divalent radical center forms bonds with two different atoms. Typical gem alkyldiyls include, but are not limited to gem methanyldiyl; gem ethyldiyls such as ethan-1,1-diyl,ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methyl-prop-2-en-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is $(C_{1-6})$ gem alkyldiyl, with $(C_{1-3})$ being particularly preferred.

"Alkyleno:" refers to a saturated or unsaturated, straight-chain or branched acyclic bivalent hydrocarbon bridge radical derived by the removal of one hydrogen atom from each of the two terminal carbon atoms of an acyclic parent alkane, alkene or alkyne. Typical alkyleno groups include, but are not limited to, methano; ethylenos such as ethano, etheno, ethyno; propylenos such as propano, propeno, prop-1,2-dieno, propyno, etc.; butylenos such as butano, 2-methyl-propano, but-1-eno, but-2-eno, 2-methyl-prop-1-eno, 2-methanylidene-propano, but-1,3-dieno, but-1-yno, but-2-yno, but-1,3-diyno, etc.; and the like. Where specific levels of saturation are intended, the nomenclature alkano, alkeno and/or alkyno is used. In preferred embodiments, the alkyleno group is $(C_{1-8})$ alkyleno, with $(C_{1-3})$ being particularly preferred. Also preferred are straight-chain saturated alkano radicals, e.g., methano, ethano, propano, butano, and the like.

"Alkylidene:" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidene, cyclopropan-1-ylidene, prop-1-en-1-ylidene, prop-2-en-1-ylidene, cycloprop-2-en-1-ylidene, etc.; butylidenes such as butan-1-ylidene, butan-2-ylidene, 2-methyl-propan-1-ylidene, cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is $(C_{1-8})$ alkylidene, with $(C_{1-3})$ being particularly preferred. Also preferred are acyclic saturated alkanylidene radicals in which the divalent radical is at a terminal carbon, e.g., methanylidene, ethan-1-ylidene, propan-1-ylidene, butan-1-ylidene, 2-methyl-propan-1-ylidene, and the like.

"Alkylidyne:" refers to a saturated or unsaturated, branched or straight-chain trivalent hydrocarbon radical derived by removal of three hydrogen atoms from the same carbon atom of a parent alkane, alkene or alkyne. The trivalent radical center forms a triple bond with a single atom. Typical alkylidyne radicals include, but are not limited to, methanylidyne; ethanylidyne; propylidynes such as propan-1-ylidyne, prop-2-en-1-ylidyne, prop-2-yn-1-ylidyne; butylidynes such as butan-1-ylidyne, 2-methyl-propan-1-ylidyne, but-2-en-1-ylidyne, but-3-en-1-ylidyne, buta-2,3-dien-1-ylidyne, but-2-yn-1-ylidyne, but-3-yn-1-ylidyne, etc.; and the like. Where specific levels of saturation are intended, the nomenclature alkanylidyne, alkenylidyne and/or alkynylidyne is used. In preferred embodiments, the alkylidyne group is $(C_{1-8})$ alkylidyne, with $(C_{1-3})$ being particularly preferred. Also preferred are saturated alkanylidyne radicals, e.g., methanylidyne, ethanylidyne, propan-1-ylidyne, butan-1-ylidyne, 2-methyl-propan-1-ylidyne, and the like.

"Heteroalkyl, Heteroalkanyl, Heteroalkenyl, Heteroalkynyl, Heteroalkylidene, Heteroalkylidyne, Heteroalkyldivi, Vic Heteralkyldiyl, Gem Heteroalkyldiyl, Heteroalkyleno and Heteroalkyldiylidene:" refer to alkyl, alkanyl, alkenyl, alkynyl, alkylidene, alkylidyne, alkyldiyl, vic alkyldiyl, gem alkyldiyl, alkyleno and alkyldiylidene radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkyl, heteroalkanyl, heteroalkenyl, heteroalkynyl, heteroalkylidene, heteroalkylidyne, heteroalkyldiyl, vic heteroalkyldiyl, gem heteroalkyldiyl, heteroalkyleno and heteroalkyldiylidene radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or $(C_1\text{-}C_6)$ alkyl.

"Parent Aromatic Ring System:" refers to an unsaturated cyclic or polycyclic ring system having a conjugated Tr electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_{5-20}$) aryl, with ($C_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is ($C_{6-26}$) arylalkyl, e.g., the alkanyl, alkenyl or alkynyl moiety of the arylalkyl group is ($C_{1-6}$) and the aryl moiety is ($C_{5-20}$). In particularly preferred embodiments the arylalkyl group is ($C_{6-13}$), e.g., the alkanyl, alkenyl or alkynyl moiety of the arylalkyl group is ($C_{1-3}$) and the aryl moiety is ($C_{5-10}$). Even more preferred arylalkyl groups are phenylalkanyls and most preferred is phenylmethyl (i.e. benzyl).

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy ($CH_3CH_2CH_2O$—), propan-2-yloxy (($CH_3)_2CHO$—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are ($C_{1-8}$) alkanyloxy groups, with ($C_{1-3}$) being particularly preferred.

"Parent Heteroaromatic Ring System:" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazine, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred. Specific preferred heteroaryls for the present invention are chromene, cinnoline, furan, imidazole, indazole, indole, indolizine, isobenzofuran, isochromene, isoindole, isoquinoline, isothiazole, isoxazole, naphthyridine, oxadiazole, oxazole, perimidine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazine, triazole.

"Substituted:" refers to a radical in which one or more hydrogen atoms are each independently replaced with the same or different substituent(s). Typical substituents include, but are not limited to, —X, —R, —O—, =O⁻, —OR, —O—OR, —SR, —S⁻, =S, —NRR, =NR, —CX$_3$, —CN, —OCN, —SCN, —NCO, —NCS, —NO, —NO$_2$, =N$_2$, —N$_3$, —NHOH, —S(O)$_2$O⁻, —S(O)$_2$OH, —S(O)$_2$R, —P(O)(O⁻)$_2$, —P(O)(OH)$_2$, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, ($C_{1-8}$ alkylamino)carbonyl, (arylamino)carbonyl and aryl($C_{1-8}$ alkyl)carbonyl.

"Aroyl" refers to arylacyl substituents.

"Acyl" refers to alkylcarbonyl substituents.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

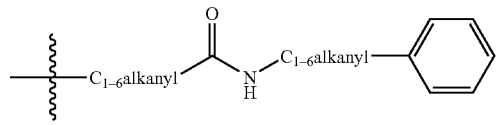

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For the purposes of this invention, the term "chemical library" means a collection of molecules prepared by the method of the invention based on logical design by means of simultaneous or parallel chemical reactions. Each species of molecule in the library is referred to as a member of the library.

Abbreviations used in the specification, particularly the Schemes and Examples, are as follows:

DIEA=Diisopropylethylamine
DMF=N,N-Dimethylformamide
DMSO=dimethylsulfoxide
Et=Ethyl (—CH$_2$CH$_3$)
Ex #=Example Number
Me=Methyl (—CH$_3$)
Ph=Phenyl (—C$_6$H$_5$)
TEA=Triethylamine
TEMPO=2,2,6,6-tetramethyl-1-piperidinyloxy free radical
TFA=Trifluoroacetic acid
THF=Tetrahydrofuran The invention is directed to a method of synthesizing 2-substituted azole compunds of formula (I):

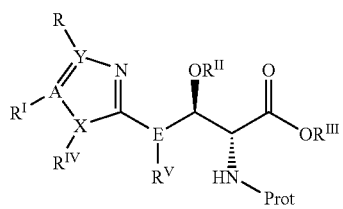
(I)

the method comprising
(a) reacting an aldehyde of formula (II)

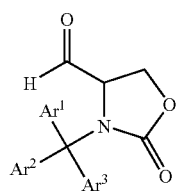
(II)

with an azole of formula (III)

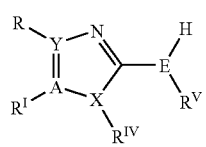
(III)

in the presence of a carbonylating agent of formula (IV)

(IV)

to give an oxazolidone of formula (Ia)

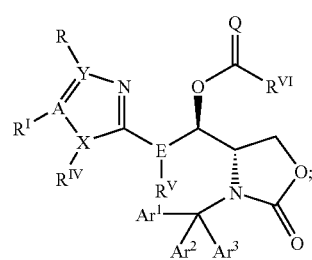
(Ia);

(b) reacting the the oxazolidone of formula (Ia) so as to hydrolyze the triarylmethyl group, cleave the O—(C=Q) bond, and open the oxazolidone, then reacting the resulting intermediate with Prot-Z wherein Prot-Z is an amino protecting agent selected from the group consisting of Prot-O-Prot, Prot-halide, Prot-N$_3$, R$^X$O$_2$C—OCO$_2$N=C(C$_6$H$_5$)CN, Prot-O-(1-benzotriazolyl), R$^X$O$_2$C—O—C$_6$F$_5$, R$^X$O$_2$C—O—C$_6$H$_4$—NO$_2$, R$^X$O$_2$C—O—CH(Cl)CCl$_3$, R$^X$O$_2$C—O-2-pyridyl, R$^X$O$_2$C—S-2-pyridyl, R$^X$O$_2$C—S—Ph, R$^X$O$_2$C—OSu, R$^X$O$_2$C-(1-imidazoyl), R$^X$O$_2$C—CN, R$^X$CO—O—C$_6$F$_5$, R$^X$CO—CN, Fmoc-Cl, Fmoc-N$_3$, Fmoc-O-(1-benzotriazolyl), Fmoc-OSu, or Fmoc-O—C$_6$F$_5$, to give an azole-containing intermediate of formula (Ib)

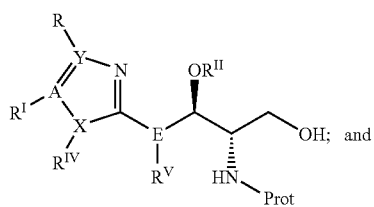
(Ib);

(c) oxidizing the intermediate of formula (Ib) to give the 2-substituted azole derivative of formula (I);

An alternative method comprises
(a) reacting an aldehyde of formula (II)

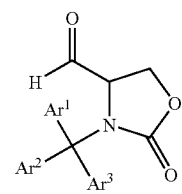
(II)

with an azole of formula (III)

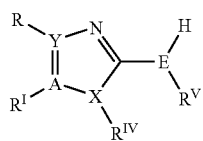

in the presence of a carbonylating agent of formula (IV)

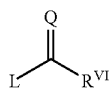

wherein Q=S and $R^{VI}$ is —$NR^{VII}R^{VIII}$, to give an oxazolidone of formula

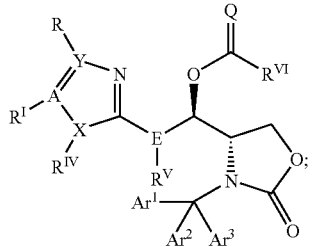

(b) reacting the oxazolidone of formula (Ia) so as to hydrolyze the triarylmethyl group, then reacting the resulting intermediate with Prot-Z wherein Prot-Z is an amino protecting agent selected from the group consisting of Prot-O-Prot, Prot-halide, Prot-$N_3$, $R^XO_2C$—$OCO_2N$=$C$ ($C_6H_5$)CN, Prot-O-(1-benzotriazolyl), $R^XO_2C$—O—$C_6F_5$, $R^XO_2C$—O—$C_6H_4$—$NO_2$, $R^XO_2C$—O—CH(Cl)$CCl_3$, $R^XO_2C$—O-2-pyridyl, $R^XO_2C$—S-2-pyridyl, $R^XO_2C$—S—Ph, $R^XO_2C$—OSu, $R^XO_2C$-(1-imidazoyl), $R^XO_2C$—CN, $R^XCO$—O—$C_6F_5$, $R^XCO$—CN, Fmoc-Cl, Fmoc-$N_3$, Fmoc-O-(1-benzotriazolyl), Fmoc-OSu, or Fmoc-O—$C_6F_5$, to give an azole-containing intermediate of formula (Ic)

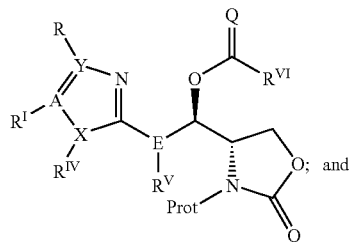

(c) reacting the intermediate of formula (Ic), so as to hydrolyze the O—(C=Q) bond and oxazolidone then oxidize the intermediate to give the 2-substituted azole of formula (I).

Another alternative method comprises
(a) reacting an aldehyde of formula (II)

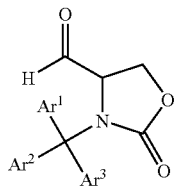

with an azole of formula (III)

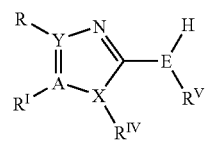

in the presence of a carbonylating agent of formula (IV)

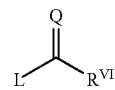

to give an oxazolidone of formula (Ia)

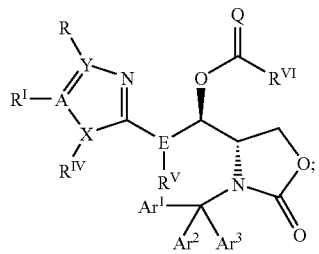

(b) reacting the oxazolidone of formula (Ia) so as to hydrolyze the triarylmethyl group, then reacting the resulting intermediate with Prot-Z wherein Prot-Z is an amino protecting agent selected from the group consisting of Prot-O-Prot, Prot-halide, Prot-$N_3$, $R^XO_2C$—$OCO_2N$=$C$ ($C_6H_5$)CN, Prot-O-(1-benzotriazolyl), $R^XO_2C$—O—$C_6F_5$, $R^XO_2C$—O—$C_6H_4$—$NO_2$, $R^XO_2C$—O—CH(Cl)$CCl_3$, $R^XO_2C$—O-2-pyridyl, $R^XO_2C$—S-2-pyridyl, $R^XO_2C$—S—Ph, $R^XO_2C$—OSu, $R^XO_2C$-(1-imidazoyl), $R^XO_2C$—CN, $R^XCO$—O—$C_6F_5$, $R^XCO$—CN, Fmoc-Cl, Fmoc-$N_3$, Fmoc-O-(1-benzotriazolyl), Fmoc-OSu, or Fmoc-O—$C_6F_5$, to give an azole-containing intermediate of formula (Ic)

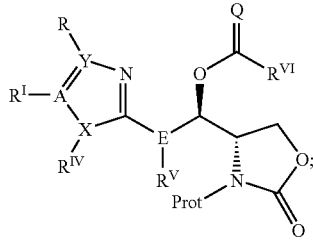

(Ic);

(c) reacting the intermediate of formula (Ic) so as to hydrolyze the O—(C=Q) bond, then reacting the intermediate with $R^{II}$-L to give an intermediate of formula (Id);

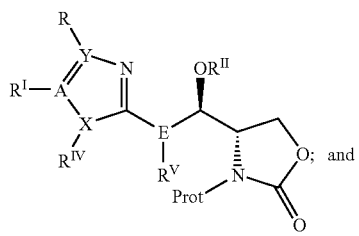

(Id); and (d) reacting the intermediate of formula (Id) so as to hydrolyze the oxazolidone group, then oxidizing the intermediate to give the 2-substituted azole of formula (I);

In the above methods, unless otherwise specified, $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy;

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ and $R^{III}$ independently are H, $C_{1-8}$heteroalkyl, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or —$NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Q is O or S;

L is Cl, Br, I, F, $OSO_2R^{IX}$, $O(CO)R^{IX}$ or $OCO_2R^{IX}$;

$R^{IX}$ is fluorinated $C_{1-8}$alkyl, $C_{1-8}$alkyl $C_{5-10}$aryl, $C_{5-10}$aryl$C_{1-8}$alkanyl, or $C_{5-10}$heteroaryl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc;

In preferred embodiments of the methods above, Prot is Boc, Fmoc, Alloc, Cbz, Ts, and Mtr.

The invention is also directed to compounds of formulas (I), (Ia), (Ib), (Ic), (Id), and (II) and to pharmaceutical compositions containing them. Thus, one aspect of the present invention is directed to 2-substituted azole compounds of formula (I):

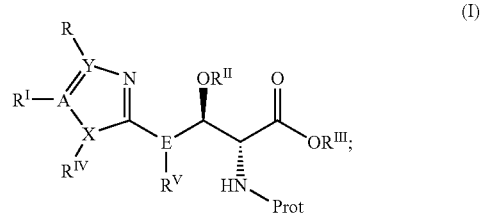

(I)

wherein

X is N or S;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ and $R^{III}$ independently are H, $C_{1-8}$heteroalkyl, $C_{1-8}$alkyl, $C_{5-10}$aryl$C_{1-8}$alkanyl or $C_{1-8}$heteroalkyl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

The invention is also directed to a compound of of formula (Ia)

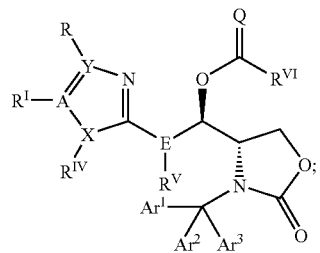

(Ia)

wherein
X is N or S;
Y and A independently are C or N;
E is a direct bond or CH;
R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or —$NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Q is O or S; and $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy.

The invention is also directed to a compound of of formula (Ib)

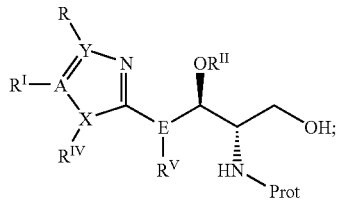

(Ib)

wherein
X is N or S;
Y and A independently are C or N;
E is a direct bond or CH;
R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VI}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ is H, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

In preferred embodiments Prot is Boc, Fmoc, Alloc, Cbz, Ts, and Mtr.

The invention is also directed to a compound of formula (Ic)

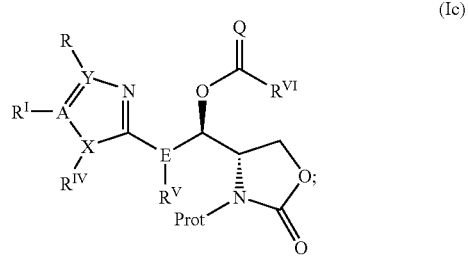

(Ic)

wherein

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or —$NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

In preferred embodiments Prot is Boc, Fmoc, Alloc, Cbz, Ts, and Mtr.

The invention is also directed to a compound of formula (Id)

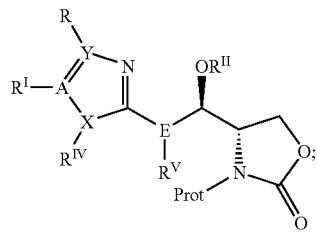

wherein

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, Wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ is H, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

In preferred embodiments Prot is Boc, Fmoc, Alloc, Cbz, Ts, or Mtr.

The invention is also directed to a compound of formula (II)

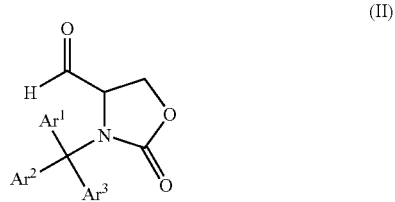

wherein $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy.

In preferred embodiments of the methods and compounds of the invention

1. Prot is Boc, Fmoc, Alloc, Cbz, Ts, or Mtr;
2. Prot is Boc or Cbz;
3. Prot is Boc;
4. $Ar^1$, $Ar^2$, and $Ar^3$ are phenyl;
5. X is N;
6. A is C;
7. Y is C;
8. X is N, A is C, and Y is C;
9. Q is S;
10. E is a direct bond and $R^V$ is absent;
11. R is H;
12. $R^I$ is H;
13. R and $R^I$ taken together are —(CH=CH)$_2$—;
14. $R^{IV}$ is $C_{1-8}$alkyl $C_{5-10}$aryl$C_{1-8}$alkanyl or $C_{5-10}$aryl$C_{1-8}$heteroalkyl;
15. $R^{IV}$ is methyl, Benzyl or —$CH_2OCH_2C_6H_5$;
16. $R^V$ is absent, or H;
17. $R^{IV}$ and $R^V$ together with E form a five to eight membered cyclic alkyl or cyclic heteroalkyl;
18. $R^{IV}$ and $R^V$ together with E form a 6 membered cyclic alkanyl;
19. $R^{VI}$ is $NMe_2$;
20. $R^{VII}$ is $C_{1-8}$alkyl;
21. $R^{VIII}$ is $C_{1-8}$alkyl;
22. $R^{VII}$ and $R^{VIII}$ taken taken together form a three to seven membered cyclic alkanyl or cyclic heteroalkanyl;
23. L is Cl, Br, $OSO_2R^{IX}$, or $O(CO)R^{IX}$;
24. $R^{IX}$ is fluorinated $C_{1-8}$alkyl, $C_{1-8}$alkyl $C_{5-10}$aryl, $C_{5-10}$aryl$C_{1-8}$alkanyl, or $C_{5-10}$heteroaryl;
25. L is Cl; and
26. combinations of 1 through 25, above.

Compounds of formulas (I), (Ia), and (Ib) may be prepared according to the method of Scheme 1.

SCHEME 1

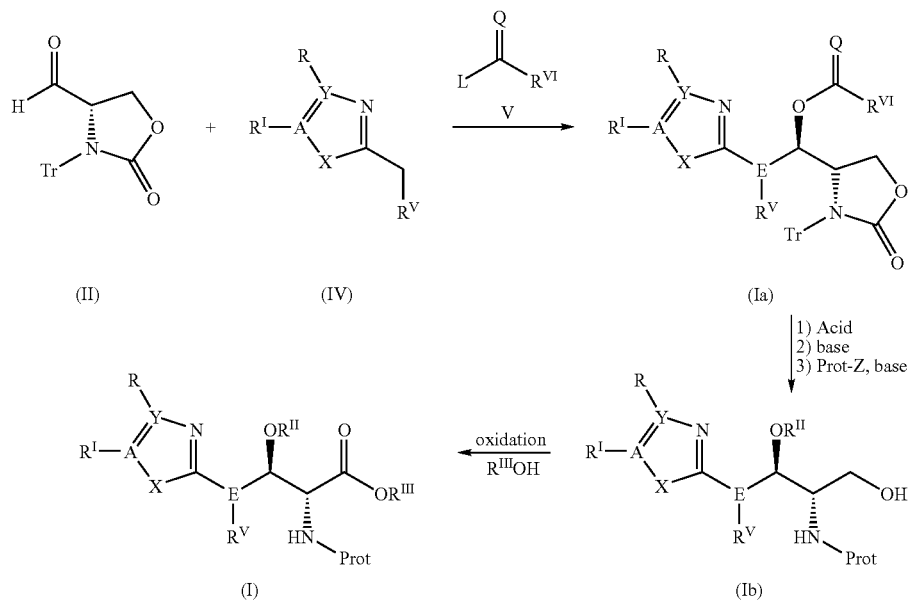

Compound II as prepared according to Scheme 4 is reacted with a 1,3-azole derivative IV in the presence of a carbonylating agent and tertiary amine base. Upon completion of the reaction and purification, the carbamate product Ia is treated with acid to cleave the triarylmethyl-oxazolidone bond. Subsequent reaction with base hydrolyses the carbamate and opens the oxazolidone to the amino alcohol. Treatment with an amino protecting agent provides intermediate Ib. The resultant intermediate is oxidized to furnish the product I.

Compounds of formulas (I) and (Ic) may be prepared according to the method of Scheme 2.

SCHEME 2

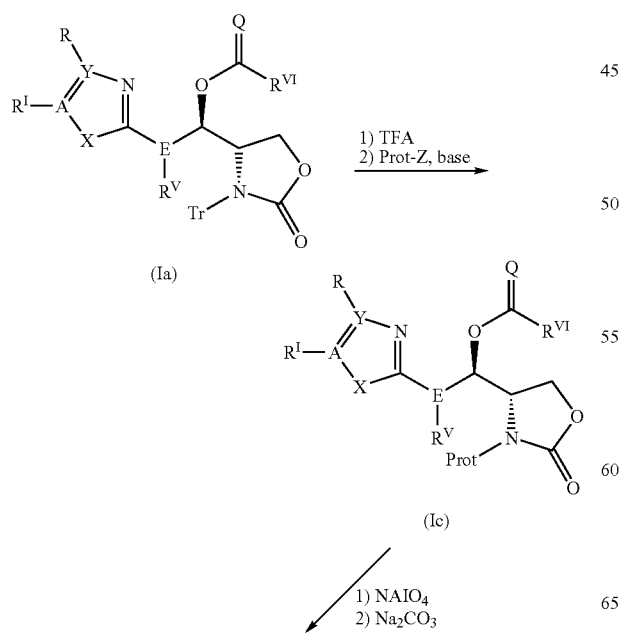

-continued

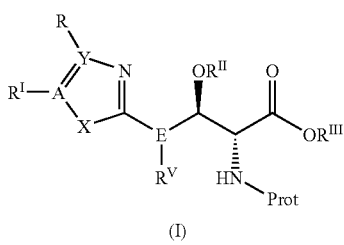

Compound Ia is treated with acid to cleave the triarylmethyl-oxazolidone bond and the intermediate is reacted with an amino protecting agent to furnish product Ic. Treatment of compound Ic with oxidant and base affords the 2-substituted azole of formula I.

Compounds of formulas (I) and (Id) may be prepared according to the method of Scheme 3.

SCHEME 3

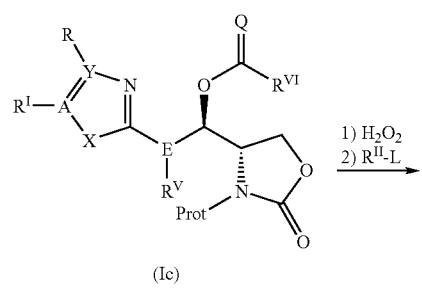

-continued

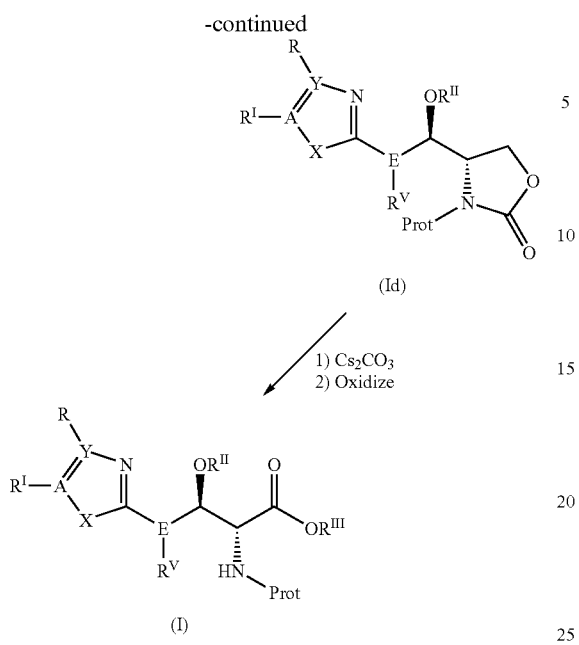

Treatment of compound Ic with oxidant and reacting the intermediate with an R"-L group provides intermediate Id. Hydrolysis of the oxazolidone in Id followed by oxidation of the intermediate provides 2-substituted azole of formula I.

Aldehydes of formula (II) may be prepared according to the process outlined in Scheme 4.

SCHEME 4

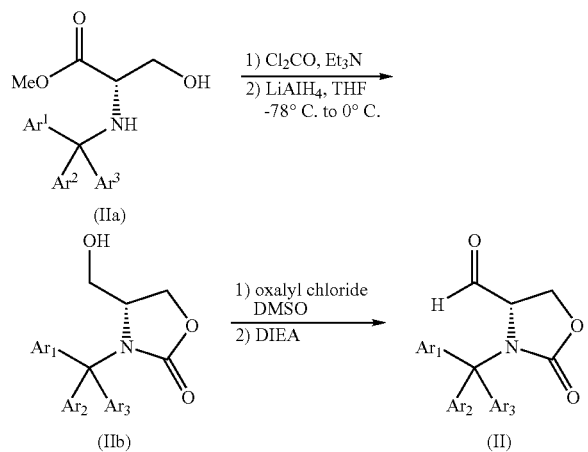

N-(Triarylmethyl)serine alkyl ester is reacted with a carbonylating agent and base to furnish an oxazolidone intermediate. The ester of this intermediate is subsequently reduced to provide the alcohol IIb. The Compound IIb is oxidized to furnish aldehyde II.

Azoles of formula (III) are commercially available or may be prepared according to methods known in the art.

The following Examples are set forth to aid in the understanding of the invention, and are not intended and should not be construed to limit in any way the invention set forth in the claims which follow thereafter.

EXAMPLE 1

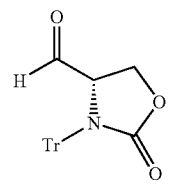

Commercially available N-tritylserine methyl ester (15.0 g, 41.5 mmol) in 350 mL toluene was stirred with triethylamine (16 mL, 115 mmol) until the solids were dissolved. A solution of phosgene (20% w/w in toluene, 25 mL, 47.2 mmol) was then added and the solution was stirred for 2 h. The mixture was then poured into 100 mL 1N HCl, and the layers separated. To the aqueous layer was then added 40 mL 3N NaOH, which was then extracted twice with 100 mL 1:1 toluene:dichloromethane. The combined organic layers were then washed once with 100 mL 1N HCl, twice with 100 mL 1N NaOH, and once with 100 mL brine. The solution was dried over sodium sulfate then passed through a pad of silica gel (0.5", 500 mL sintered glass funnel). The silica was washed with 250 mL ethyl acetate and concentrated under vacuum to afford a crude foam (16.5 g, >100%).

The above prepared solid was dissolved in 300 ml dry THF and cooled in a dry ice-2-propanol bath to an internal temperature of −65° C. A solution of lithium aluminum hydride (1M in THF, 50 mL) was then added dropwise over 45 min. After an additional 15 min, the solution was allowed to slowly warm to −10° C. over 45 min before being recooled to −45° C., at which time excess hydride was quenched by the addition of 25 mL ethyl acetate, followed by the addition of 2.5 mL water, 2.5 mL 3N NaOH, then 7.5 mL water. The solution was stirred 1 h at ambient temperature before a saturated solution of sodium-potassium tartrate (40 mL) was added. The mixture was stirred 30 min then decanted through diatomaceous earth. The solids were washed with 100 mL water, then twice with 100 mL ethyl acetate. A saturated solution of sodium bicarbonate (150 mL) was added and the layers were separated, then the aqueous layer extracted twice with 100 mL ethyl acetate. The combined organic layers were washed once with 100 mL saturated sodium-potassium tartrate and once with 150 mL brine, dried over sodium sulfate and concentrated under vacuum to afforded alcohol IIIb (14.4 g, 97%) as a yellow foam.

A solution of oxallyl chloride (1.4 mL, 16 mmol) in 60 mL dichloromethane was cooled to −78° C. then treated with DMSO (2.2 mL, 31 mmol). After 20 min, a solution of alcohol IIIb (3.61 g, 1.0 mmol) in 20 mL dichloromethane was added dropwise over 20 min. After stirring an additional 40 min, DIEA (10.6 mL, 61 mmol) was added, stirred for 15 min then allowed to warm to ambient temperature. The solution was poured into 100 mL 1N HCl, separated and the aqueous phase was extracted twice with 50 mL dichloromethane. The combined organic phases were washed twice with 50 mL saturated sodium bicarbonate, once with 50 mL brine, dried over sodium sulfate, then concentrated under vacuum. The light tan foam was dissolved in 10 mL ethyl acetate before the addition of 200 mL hexanes. The solids that precipitated were triturated overnight, filtered and washed twice with 100 mL hexanes. After being dried under vacuum, compound 1 was isolated as a light tan solid (2.99 g, 84%).

EXAMPLE 2

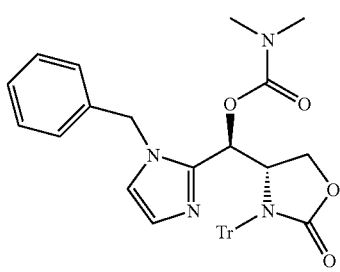

Compound 1 (450 mg, 1.25 mmol) and 1-benzylimidazole (159 mg, 1.0 mmol) were dissolved in 5 mL acetonitrile. N,N-Dimethylcarbamoyl chloride (0.125 mL, 1.35 mmol) and N,N-diisopropylethylamine (0.53 mL, 3.0 mmol) were then added. After stirring for 3 days, the solution was poured into 10 mL water and 20 mL dichloromethane. The layers were separated and the aqueous layer was extracted with an additional 10 mL dichloromethane. The combined organic extracts were washed once with 20 mL 1N sodium hydroxide and once with 20 mL brine, dried over sodium sulfate and purified on silica gel column chromatography with a mixture of 10% ethyl acetate in hexanes to 75% ethyl acetate. Compound 2 was isolated as an off-white foam, 420 mg (72% yield).

HRMS: 587.2662 (calc. 587.2658 for MH$^+$).

EXAMPLE 3

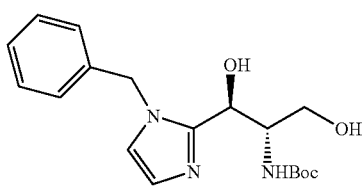

Compound 2 (600 mg, 1.02 mmol) was dissolved in a solution of 1% water in trifluoroacetic acid and stirred at ambient temperature until the cleavage of the trityl group was complete. The solution was concentrated under vacuum then the crude intermediate was dissolved in 18 mL of a 2:1 solution of ethanol:water. Solid potassium hydroxide (2.0 g, 30 mmol) was added and the solution was heated to reflux for 18 hours. The intermediate was extracted by acidification of the solution with conc. hydrochloric acid and partitioning between 30 mL diethyl ether and 20 mL water. Separation of the layers and extraction of the organic layer with 20 mL 1N hydrochloric acid was followed by neutralization of the combined aqueous extracts with solid sodium bicarbonate. 1,4-Dioxane (25 mL) was added to the aqueous solution followed by potassium hydroxide (560 mg, 8.5 mmol) and di-tert-butyidicarbonate (0.3 mL, 1.3 mmol). The solution was stirred at ambient temperature for 1 h, then heated to reflux for 20 min, cooled then extracted 3 times with 50 mL dichloromethane. The organic extract was washed with 50 mL brine, dried over sodium sulfate and concentrated under vacuum. Purification of the crude product by silica gel column chromatography using a gradient of 0-5% methanol in ethyl acetate provides the Compound 3 (140 mg, 40% yield).

HRMS: 348.1927 (calc. 348.1923 for MH$^+$).

EXAMPLE 4

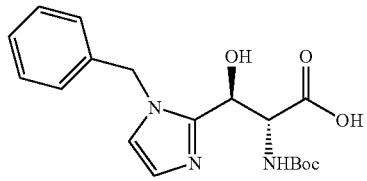

Compound 3 (17 mg, 0.049 mmol), TEMPO (2 mg, 0.012 mmol) and sodium chlorite (16 mg, 0.142 mmol) were dissolved in a mixture of 0.5 mL acetonitrile and 0.5 mL phosphate buffer (0.5M, pH=6.8). A solution of bleach (6% aqueous, 0.06 mL, 0.049 mmol, diluted to 0.25 mL with water) was added via syringe pump to the solution at a rate of 0.01 mL/h at a temperature of 45° C. After 24 h, the pH of the solution was adjusted to pH=9 with 1N NaOH and diethyl ether was added (2 mL). The layers are separated and the organic layer was extracted once with 2 mL 1N NaOH. The combined aqueous extracts are acidified to pH=3 with conc. hydrochloric acid, saturated with solid sodium chloride then extracted 5 times with 5 mL ethyl acetate. The combined organic extracts were concentrated in vacuo to furnish compound 4 (10 mg, 56%).

HRMS: 362.1732 (calc. 362.1716 for MH$^+$).

EXAMPLE 5

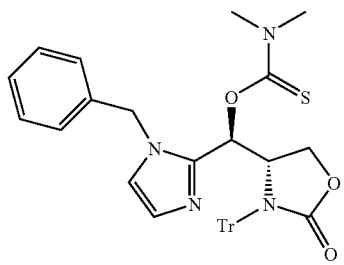

Compound 1 (1.79 g, 5 mmol) and 1-benzylimidazole (0.95 g, 6 mmol) were dissolved in 20 mL acetonitrile. N,N-Dimethylthiocarbamoyl chloride (0.95 g, 7.7 mmol) and triethylamine (2.2 mL, 15.8 mmol) were then added. After stirring for 5 days, the solution was poured into 20 mL saturated sodium bicarbonate solution, and extracted 3 times with 20 mL ethyl acetate. The combined organic extracts were washed once with 20 mL brine, dried over sodium sulfate, concentrated and purified on silica gel column chromatography with a mixture of 0%-100% ethyl acetate in hexanes. Compound 5 was isolated as an off-white foam, 2.20 g (73% yield).

HRMS: 603.2437 (calc. 603.2430 for MH$^+$).

EXAMPLE 6

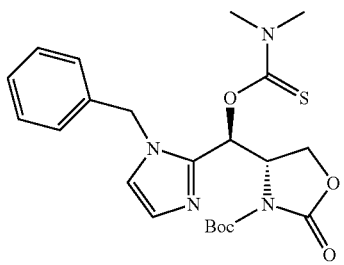

Compound 5 (940 mg, 1.5 mmol) was dissolved in a 10:1 solution of trifluoroacetic acid:water (6.6 mL) and stirred at ambient temperature until the cleavage of the trityl group was complete (4-24 h). The solution was concentrated under vacuum, azeotroped with toluene and the resultant foam dissolved in DMF (10 mL). Potassium carbonate (3.0 g, 21.7 mmol) was added, the solution stirred for 20 min then 4-dimethylaminopyridine was added (17 mg, 0.14 mmol) followed by di-tert-butyldicarbonate (0.6 mL, 2.6 mmol). After 5 h, the solution was poured into 30 mL water and extracted 4 times with 20 mL ethyl acetate. The combined organic extracts were washed once with 20 mL brine, dried over sodium sulfate and concentrated under vacuum. Purification on silica gel using a gradient elution of 25%-100% ethyl acetate in hexanes afforded compound 6 as a white foam (625 mg, 91%).

HRMS: 461.1870 (calc. 461.1859 for MH$^+$).

EXAMPLE 7

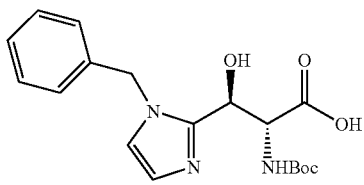

Compound 6 (46 mg, 0.1 mmol) was dissolved in 4 mL methanol. Water (0.2 mL) was added, followed by sodium periodate (90 mg, 0.42 mmol). The solution was heated at 45° C. for 8-15 h until the starting material was consumed. Sodium carbonate (91 mg, 0.86 mmol) was then added and heating was continued for an additional 4 h. The solution was diluted with 5 mL water and extracted 4 times with 10 mL ethyl acetate. The combined organic extracts are dried over sodium sulfate and concentrated under vacuum. Compound 4 was isolated following purification by reverse phase HPLC (18 mg, 50% yield) as a white gum.

EXAMPLE 8

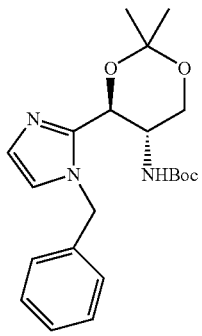

Compound 3 (16 mg, 0.46 mmol) and p-toluenesulfonic acid monohydrate (1 mg, 0.05 mmol) were dissolved in 0.5 mL toluene. 2,2-Dimethoxypropane (0.5 mL) was added and the mixture was heated at 100° C. until the starting material was consumed. The reaction mixture was cooled to ambient temperature, diluted with 10 mL ether and washed once with 10 mL 1N NaOH, once with 10 mL 0.5 N HCl, and once with 10 mL brine. The aqueous extracts were further extracted three times with dichloromethane (10 mL each), and the combined organic phases were dried over sodium sulfate and concentrated under vacuum. The product was isolated as a white foam (17 mg, 95% yield). Analysis of the 1H-NMR spectrum permitted the determination of the relative configuration. When Compound 3 is observed in a chair confirmation, the value of the $^1$H-$^1$H coupling constant between the CHO and CHN protons is indicative of a trans-relationship.

EXAMPLES 9-13

Selected compounds listed in Table 1 were prepared following the procedure outlined in Example 5 with appropriate selection and substitution of reagents, as listed in Table 2.

TABLE 1

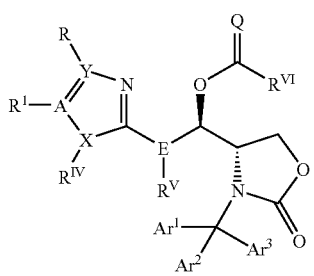

| Ex # | X | A | Y | Q | E | R | R$^I$ | R$^{IV}$ | R$^V$ | R$^{VI}$ | Ar$^1$ | Ar$^2$ | Ar$^3$ |
|---|---|---|---|---|---|---|---|---|---|---|---|---|---|
| 9 | N | C | C | S | direct bond | H | H | CH$_2$OBn | absent | NMe$_2$ | Ph | Ph | Ph |
| 10 | N | C | C | S | direct bond | —(CH=CH)$_2$— | | Me | absent | NMe$_2$ | Ph | Ph | Ph |

TABLE 1-continued

| Ex # | X | A | Y | Q | E | R | R$^I$ | R$^{IV}$ | R$^V$ | R$^{VI}$ | Ar$^1$ | Ar$^2$ | Ar$^3$ |
|---|---|---|---|---|---|---|---|---|---|---|---|---|---|
| 11 | N | C | C | S | direct bond | H | H | Me | absent | NMe$_2$ | Ph | Ph | Ph |
| 12 | N | C | C | S | CH | H | H | Me | H | NMe$_2$ | Ph | Ph | Ph |
| 13 | N | C | C | S | CH | H | H | —(CH$_2$)$_3$— | | NMe$_2$ | Ph | Ph | Ph |

TABLE 2

| | Preparation Conditions | | | |
|---|---|---|---|---|
| Ex # | Reaction Temp (° C.) | Reaction Time (h) | Yield (%) | HRMS (calc. MH$^+$) |
| 9 | 25 | 120 | 77 | 633.2526 (633.2536) |
| 10 | 25 | 120 | 60 | 577.2285 (577.2273) |
| 11 | 25 | 120 | 75 | 527.2 (527.2117) |
| 12 | 25 | 120 | 45 | 541.2271 (541.2273) |
| 13 | 25 | 72 | 20 | 567.2444 (567.2430) |

EXAMPLES 14-19

Selected compounds listed in Table 3 were prepared following the procedure outlined in Example 6, with appropriate selection and substitution of reagents, as listed in Table 4.

TABLE 3

| Ex # | X | A | Y | Q | E | R | R$^I$ | R$^{IV}$ | R$^V$ | R$^{VI}$ | Prot |
|---|---|---|---|---|---|---|---|---|---|---|---|
| 14 | N | C | C | S | direct bond | H | H | CH$_2$OBn | absent | NMe$_2$ | Boc |
| 15 | N | C | C | S | direct bond | —(CH=CH)$_2$— | | Me | absent | NMe$_2$ | Boc |
| 16 | N | C | C | S | direct bond | H | H | Me | absent | NMe$_2$ | Boc |
| 17 | N | C | C | S | direct bond | H | H | Bn | absent | NMe$_2$ | Cbz |
| 18 | N | C | C | S | CH | H | H | Me | H | NMe$_2$ | Boc |
| 19 | N | C | C | S | CH | H | H | —(CH$_2$)$_3$— | | NMe$_2$ | Boc |

TABLE 4

| | Preparation Conditions | | | |
|---|---|---|---|---|
| Ex # | Base, Prot-Z | Reaction Temp (° C.) | Reaction Time (h) | Yield (%) | HRMS (calc. MH$^+$) |
| 14 | K$_2$CO$_3$, Boc$_2$O | 25 | 24 | 73 | 491.1953 (491.1964) |
| 15 | K$_2$CO$_3$, Boc$_2$O | 25 | 1 | 75 | 435.1698 (435.1702) |
| 16 | K$_2$CO$_3$, Boc$_2$O | 25 | 24 | 70 | 385.1554 (385.1546) |
| 17 | NaH, Cbz-Cl | 25 | 1 | 65 | 495.1709 (495.1702) |
| 18 | K$_2$CO$_3$, Boc$_2$O | 25 | 18 | 79 | 399.1702 (399.1702) |
| 19 | K$_2$CO$_3$, Boc$_2$O | 25 | 2 | 80 | 425.1869 (425.1859) |

Selected spectral data for compounds of the invention are listed in Table 5.

TABLE 5

| Ex # | Structure | Spectral Data |
|---|---|---|
| 1 | 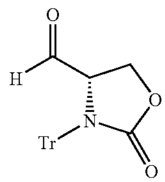 | ¹H-NMR (CDCl₃, 400 MHz) δ 9.23 (d, 1H, J=3.1 Hz), 7.32 (m, 15H), 4.51(dd, 1H, J=9.5, 9.5 Hz), 4.37(ddd, 1H, J=3.1, 4.5, 9.5 Hz), 4.22(dd, 1H, J=4.5, 9.2 Hz); ¹³C-NMR(CDCl₃, 100 MHz) δ 197.0, 156.8, 141.7, 130.0, 128.2, 128.1, 74.3, 64.3, 62.9; |
| 5 | 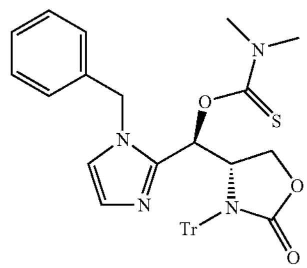 | ¹H-NMR (CDCl₃, 400 MHz) δ 7.35–7.30(m, 9H), 7.27–7.22(m, 6H), 7.21–7.16(m, 3H), 7.00(m, 2H), 6.91(d, 1H, J=1.2 Hz), 6.43 (d, 1H, J=1.2 Hz), 6.06(s, 1H), 5.67(d, 1H, J=8.9 Hz), 4.82(d, 1H, J=15.1 Hz) 4.56 (t, 1H, J=8.6 Hz), 4.51(d, 1H, J=8.6 Hz) 4.12(d, 1H, J=15.0 Hz), 3.36(s, 3H), 3.12 (s, 3H); ¹³C-NMR (CDCl₃, 100 MHz) δ 186.3, 158.2, 142.9, 142.4, 135.6, 130.5,128.8, 128.5 128.2, 127.9, |
| 6 | 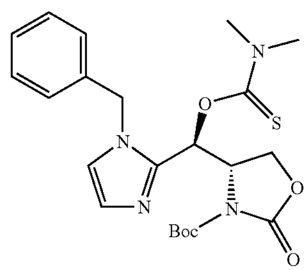 | ¹H-NMR (CDCl₃, 400 MHz) δ 7.44(d, 1H, J=1.2 Hz), 7.34–7.26(m, 2H), 7.07–7.03(m, 3H), 6.97(d, 1H, J=1.2 Hz), 5.45(d, 1H, J=16.1 Hz), 5.01–4.94(m, 2H), 4.59(m, 1H), 3.18(s, 3H), 2.78(s, 3H), 1.52(s, 9H); ¹³C-NMR (CDCl₃, 100 MHz) δ 186.7, 152.1, 149.1, 142.8, 136.8, 128.7, 128.5, 127.9, 126.5, 122.3, 84.4, 71.2, 64.0, 57.1, 49.7, 43.4, 37.7, 28.1; |
| 9 | 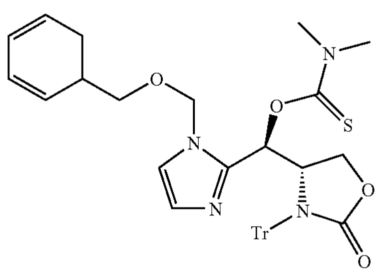 | ¹H-NMR (CDCl₃, 400 MHz) δ 7.37–7.19(m, 20H), 7.04(d, 1H, J=1.2 Hz), 6.92(d, 1H, J=1.2 Hz), 6.00(s, 1H), 5.36(d, 1H, J=9.0 Hz), 5.26(s, 1H), 4.78(d, 1H, J=10.5 Hz), 4.67(d, 1H, J=10.5 Hz), 4.46(d, 1H, J=8.8 Hz), 4.38(t, 1H, J=8.9 Hz), 4.31(d, 1H, J=14.3 Hz), 4.28(d, 1H, J=14.3 Hz), 3.36 (s, 3H), 3.17(s, 3H); ¹³C-NMR (CDCl₃, 100 MHz) δ 185.8, 157.8, 142.4, 142.1, 136.4, 130.2, 128.5, 128.1, 127.7 |
| 10 | 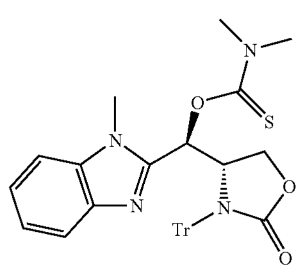 | ¹H-NMR (CDCl₃, 400 MHz) δ 7.69(m, 1H), 7.36–7.19(m, 18H), 6.01(s, 1H), 5.89(d, 1H, J=8.9 Hz), 4.53(t, 1H, J=8.6 Hz), 4.48(d, 1H, J=8.4 Hz), 3.35(s, 3H) 3.17 (s, 3H), 3.13(s, 3H); ¹³C-NMR (CDCl₃, 100 MHz) δ 186.3, 157.7, 149.0, 142.3, 142.3, 135.1, 130.4, 127.8, 127.4, 123.1, 122.3, 120.0, 109.6, 74.0, 72.6, 63.3, 59.0, 43.2, 38.6, 30.0 |
| 12 | 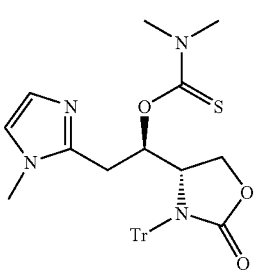 | ¹H-NMR (CDCl₃, 400 MHz) δ 7.21–7.08(m, 15H), 6.80(d, 1H, J=1.1 Hz), 6.69(d, 1H, J=1.1 Hz), 4.73(t, 1H, J=9.0 Hz), 4.68(dd, 1H, J=4.2, 11.1 Hz), 4.62(d, 2H), J=8.0 Hz), 3.47(s, 3H), 3.40(s, 3H), 3.23(dd, 1H, J=4.2, 14.3Hz), 3.15(s, 3H), 2.69(dd, 1H, J=11.1, 14.3 Hz); ¹³C-NMR (CDCl₃, 100 MHz) δ 186.9, 158.0, 142.3, 142.2, 130.5, 127.9, 127.8, 127.5, 121.7, 78.2, 74.2, 63.3, 57.2, 43.4, 38.6, 33.8, 28. |

TABLE 5-continued

| Ex # | Structure | Spectral Data |
|---|---|---|
| 13 | 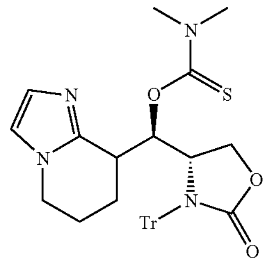 | ¹H-NMR (CDCl₃, 400 MHz) δ 7.25–7.13(m, 15H), 6.88(d, 1H, J=1.2 Hz), 6.74(d, 1H, J=1.2 Hz), 5.16(d, 1H, J=10.6 Hz), 4.83 (m, 1H), 4.76(m, 2H), 3.82(dd, 1H, J=5.6, 12.2 Hz), 3.70(dt, 1H, J=5.2, 12.2 Hz), 3.49(s, 3H), 3.27(s, 3H), 3.06(m, 1H), 2.08 (m, 1H), 1.91(m, 1H), 1.69(m, 1H) 1.52 (dddd, 1H, J=2.8, 5.6, 13.8, 13.8 Hz), ¹³C-NMR (CDCl₃, 100 MHz) δ 188.0, 158.8, 141.7, 130.5, 127.7, 127.3, 127.0,118.7, 141,7 130.5, 127.7, 127.3, 127.0, 118.7, 79.4, 75.1, 63.8, 57.8, 44.6, 43.6, 38.2, 36.6, 21.8, 19.1 (one aromatic signal missing due to signal overlap); |
| 14 | 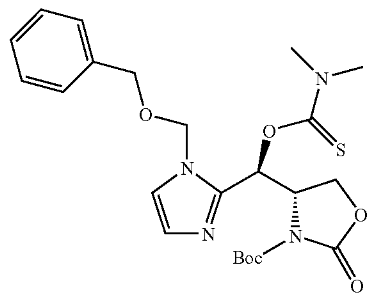 | ¹H-NMR (CDCl₃, 400 MHz) δ 7.37–7.27(m, 5H), 7.07(d, 1H, J=1.2 Hz), 7.05(d, 1H, J=1.2 Hz), 5.72(d, 1H, J=10.6 Hz), 5.45(d, 1H, J=10.6 Hz), 5.18(dd, 1H, J=3.0, 9.8 Hz), 4.80(ddd, 1H, J=1.8, 2.8, 8.8 Hz), 4.55(ddd, 1H, J=11.6, 11.6, 18.9,), 4.47(t, 1H, J=9.2 Hz), 3.29(s, 3H), 3.08(s, 3H), 1.57(s, 9H); ¹³C-NMR (CDCl₃, 100 MHz) δ 186.2, 152.2, 142.9, 136.5, 128.6, 128.5, 128.2, 127.8, 121.4, 84.6, 74. |
| 15 | 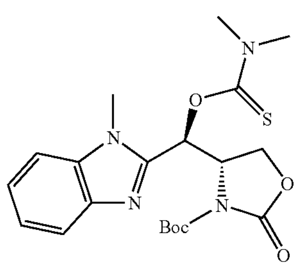 | ¹H-NMR (CDCl₃, 400 MHz) δ 7.74(d, 1H, J=7.9 Hz), 7.42(d, 1H, J=1.6 Hz), 7.39(d, 1H, J=8.4 Hz), 7.34(dd, 1H, J=1.2, 7.0 Hz), 7.32(dd, 1H, J=1.4, 3.6Hz), 7.28(dd, 1H, J=1.2, 7.0 Hz), 5.25(dd, 1H, J=2.8, 9.8 Hz), 4.91(ddd, 1H, J=1.6, 2.8, 8.9 Hz), 4.57(t, 1H, J=9.2 Hz), 3.95(s, 3H), 3.73 (s, 1H), 3.36(s, 3H), 1.60(s, 9H); ¹³C-NMR (CDCl₃, 100 MHz) δ 186.3, 152.0, 149.1, 148.6, 142.2, 135.7, 123.6, 122.6 |
| 16 | 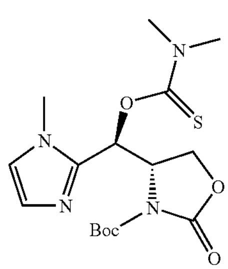 | ¹H-NMR (CDCl₃, 400 MHz) δ 7.21(d, 1H, J=1.6 1.6 Hz), 6.99(d, 1H, J=1.1 Hz), 6.89(d, 1H, J=1.1 Hz), 5.22(dd, 1H, J=2.8, 9.6 Hz), 4.75(ddd, 1H, J=1.6, 2.8, 8.9 Hz), 3.82(s, 3H), 3.39(s, 3H), 3.16(s, 3H), 1.59 (s, 9H); ¹³C-NMR (CDCl₃, 100 MHz) δ 186.5, 152.1, 149.2, 142.6, 128.4, 122.3, 84.6, 70.8, 63.5, 57.3, 43.5, 38.2, 33.7, 28.2; |
| 17 | 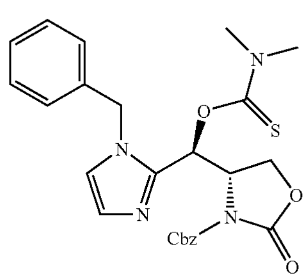 | ¹H-NMR (CDCl₃, 400 MHz) δ 7.44–7.39(m, 3H), 7.35–7.25(m, 5H), 7.05–6.98(m, 3H), 6.93(d, 1H, J=1.2 Hz), 5.33(d, 1H, J=16.0 Hz), 5.28(s, 2H), 5.17(d, 1H, J=16.0 Hz), 5.07(dd, 1H, J=3.0, 9.8 Hz), 4.95 (ddd, 1H, J=1.5, 3.0, 8.9 Hz), 4.59(1, 1H, J=8.9 Hz), 3.17(s, 3H), 2.78(s, 3H); ¹³C-NMR (CDCl₃, 100 MHz) δ 185.9, 151.7, 150.3, 142.3, 136.5, 134.8, 128.6, 128.6, 128.5, 128.5, 128.4, 127.8, 126.5, 122.1, |

TABLE 5-continued

| Ex # | Structure | Spectral Data |
|---|---|---|
| 18 | 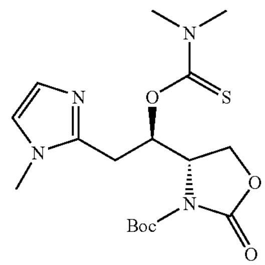 | $^1$H-NMR (CDCl$_3$, 400 MHz) δ 6.94(d, 1H, J=1.2 Hz), 6.85(d, 1H, J=1.2 Hz), 5.96 (ddd, 1H, J=1.2, 4.2, 10.9 Hz), 4.71(ddd, 1H, J=1.5, 4.2, 7.2 Hz), 4.49(m, 1H), 3.82 (s, 3H), 3.44(dd, 1H, J=4.2, 14.5 Hz), 3.45 (s, 3H), 3.12(s, 3H), 2.96(dd, 1H, J=10.9, 14.5 Hz), 1.41(s, 9H); $^{13}$C-NMR (CDCl$_3$, 100 MHz) δ 186.4, 152.5, 148.2, 142.4, 129.6, 127.7, 121.6, 11 |
| 19 | 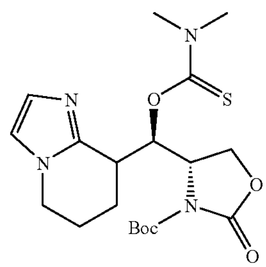 | $^1$H-NMR (CDCl$_3$, 400 MHz) δ 7.16(s, 1H), 6.95(s, 1H), 6.41(d, 1H, J=11 Hz), 5.01 (d, 1H, J=8.3 Hz), 4.63(dd, 1H, J=2.5,9.5 Hz), 4.55(dd, 1H, J=9.0, 9./0 Hz), 4.16 (ddd,1H, J=3.0, 6.0, 12.5), 3.97(dddd, 1H, J=5.4, 5.4, 10.8, 10.8 Hz), 3.60(m, 1H), 3.37(s, 3H), 3.18(s, 3H), 2.52(m, 1H), 2.13 (dddd, 1H, J=3.0, 3.0, 6.0, 13.8 Hz), 1.99 (m, 1H), 1.88(m, 1H), 1.40(s, 9H); $^{13}$C-NMR (CDCl$_3$, 100 MHz) δ 187.3,151.9, 148.3, 142.4, 125.3, 119.7, 83.8, 77.0 (CH—O, comfirmed by HMQC), 62.5, 56.5, 45.3, 43.7, 37.9, 34.7, 27.9, 22.0, 19.3; |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The compounds of the invention are useful as intermediates in the sythesis of biologically important targets such as antimicrobial agents.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

The compounds according to this invention possess two or more chiral centers, they exist as enantiomers and diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The processes for the preparation of the compounds according to the invention may give rise to products with tautomeric structural forms; wherein, the structures differ in the point of attachment of a hydrogen atom and exist in an equilibrium favoring the weaker acid. Such products include both keto-enol tautomers and imine-enamine tautomers and are intended to be encompassed within the scope of this invention. Keto-enol tautomers refer to those compound structures wherein a hydroxy atom bonded to an alkenyl carbon (the stronger acid "enol" structure) exists in equilibrium with an oxygen atom bonded by a double-bond to an alkanyl carbon (the weaker acid "keto" structure). Imine-enamine tautomers refer to those compound structures wherein a hydrogen substituted nitrogen atom bonded to an alkenyl carbon (the stronger acid "enamine" structure) exists in equilibrium with a nitrogen atom bonded via a double-bond to an alkanyl carbon (the weaker acid "imine" structure).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) or of Formula (II) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) or Formula (II) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as vanilloid receptor modulators is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

We claim:
1. A method of synthesizing 2-substituted azole compounds of formula (I):

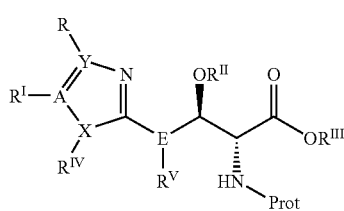

the method comprising
(a) reacting an aldehyde of formula (II)

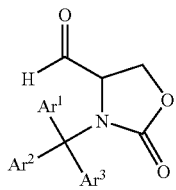

with an azole of formula (III)

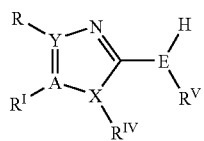

in the presence of a carbonylating agent of formula (IV)

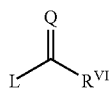

to give an oxazolidone of formula (Ia)

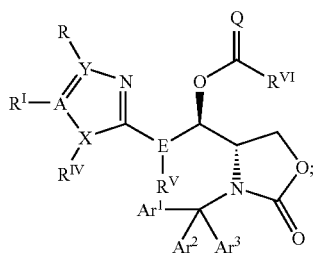

(b) reacting the the oxazolidone of formula (Ia) so as to hydrolyze the triarylmethyl group, cleave the O—(C=Q) bond, and open the oxazolidone, then reacting the resulting intermediate with Prot-Z wherein Prot-Z is an amino protecting agent selected from the group consisting of Prot-O-Prot, Prot-halide, Prot-N$_3$, R$^X$O$_2$C—OCO$_2$N=C(C$_6$H$_5$)CN, Prot-O-(1-benzotriazolyl), R$^X$O$_2$C—O—C$_6$F$_5$, R$^X$O$_2$C—O—C$_6$H$_4$—NO$_2$, R$^X$O$_2$C—O—CH(Cl)CCl$_3$, R$^X$O$_2$C—O-2-pyridyl, R$^X$O$_2$C—S-2pyridyl, R$^X$O$_2$C—S-Ph, R$^X$O$_2$C—OSu, R$^X$O$_2$C-(1-imidazoyl), R$^X$O$_2$C—CN, R$^X$CO—O—C$_6$F$_5$, R$^X$CO—CN, Fmoc-Cl, Fmoc-N$_3$, Fmoc-O-(1-benzotriazolyl), Fmoc-OSu, or Fmoc-O—C$_6$F$_5$, to give an azole-containing intermediate of formula (Ib)

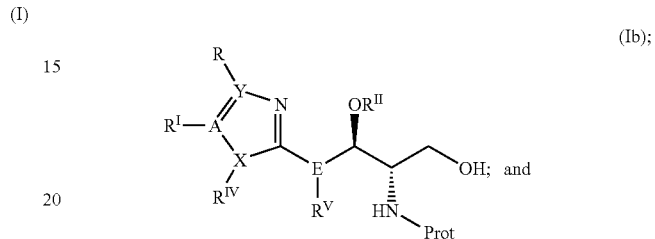

(c) oxidizing the intermediate of formula (Ib) to give the 2-substituted azole derivative of formula (I);
wherein
Ar$^1$, Ar$^2$ and Ar$^3$ independently are phenyl or phenyl optionally substituted with halogen, $C_{1-8}$alkyl, $C_{1-8}$alkyloxy, nitro, $C_{1-8}$alkylamino, nitrile, or benzoyloxy;
X is N or S;
Y and A independently are C or N;
E is a direct bond or CH;
R and R$^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —NR$^{VII}$R$^{VIII}$, —OR$^{VII}$, —COR$^{VII}$—COOR$^{VII}$—CONR$^{VII}$R$^{VIII}$ or taken together form a five to eight membered carbocyclic or heterocyclic saturated or unsaturated ring, wherein the heteroaryl in any heteroaryl-containing R or R$^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;
R$^{II}$ and R$^{III}$ independently are H, $C_{1-8}$heteroalkyl, $C_{1-8}$alkyl, $C_{5-10}$aryl$C_{1-8}$alkanyl or $C_{1-8}$heteroalkyl;
R$^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with R$^V$ forms a five to eight membered cyclic alkanyl or cyclic heteroalkanyl, wherein the heteroaryl in any heteroaryl-containing R$^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or $—NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Q is O or S;

L is Cl, Br, I, F, $OSO_2R^{IX}$, $O(CO)R^{IX}$ or $OCO_2R^{IX}$;

$R^{IX}$ is fluorinated $C_{1-8}$alkyl, $C_{1-8}$alkyl $C_{5-10}$aryl, $C_{5-10}$aryl$C_{1-8}$alkanyl, or $C_{5-10}$heteroaryl, Prot is an amino protecting group selected from the group consisting of $—CO_2R^X$, $—COR^X$, and $—SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

2. A method of synthesizing 2-substituted azole compounds of formula (I):

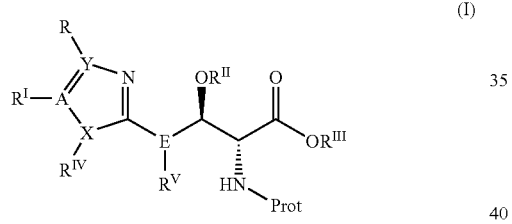
(I)

the method comprising
(a) reacting an aldehyde of formula (II)

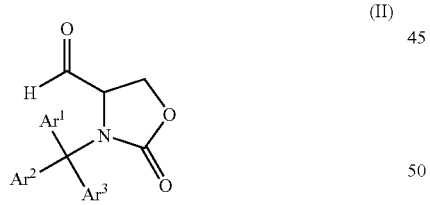
(II)

with an azole of formula (III)

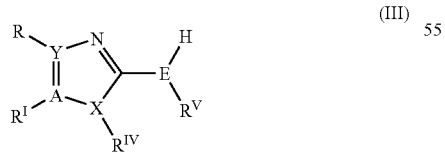
(III)

in the presence of a carbonylating agent of formula (IV)

(IV)

wherein Q=S and $R^{VI}$ is $—NR^{VII}R^{VIII}$, to give an oxazolidone of formula (Ia)

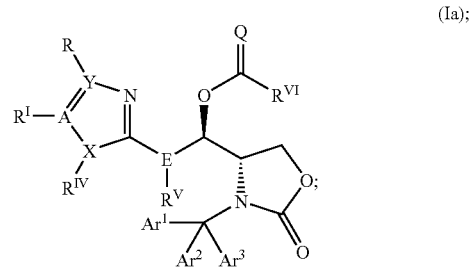
(Ia);

(b) reacting the oxazolidone of formula (Ia) so as to hydrolyze the triarylmethyl group, then reacting the resulting intermediate with Prot-Z wherein Prot-Z is an amino protecting agent selected from the group consisting of Prot-O-Prot, Prot-halide, Prot-$N_3$, $R^XO_2C—OCO_2N=C(C_6H_5)CN$, Prot-O-(1-benzotriazolyl), $R^XO_2C—O—C_6F_5$, $R^XO_2C—O—C_6H_4—NO_2$, $R^XO_2C—O—CH(Cl)CCl_3$, $R^XO_2C—O$-2-pyridil, $R^XO_2C$—S-2-pyridyl, $R^XO_2C$—S-Ph, $R^XO_2C—OSu$, $R^XO_2C$-(1-imidazoyl), $R_XO_2C—CN$, $R^XCO—O—C_6F_5$, $R^XCO—CN$, Fmoc-Cl, Fmoc-$N_3$, Fmoc-O-(1-benzotriazolyl), Fmoc-OSu, or Fmoc-O—$C_6F_5$, to give an azole-containing intermediate of formula (Ic)

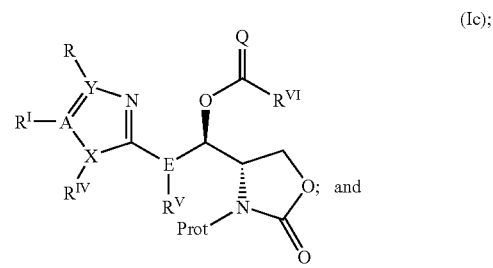
(Ic);
and (c) reacting the intermediate of formula (Ic), so as to hydrolyze the O—(C=Q) bond and oxazolidone then oxidize the intermediate to give the 2-substituted azole of formula (I);

wherein $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy;

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, $—NR^{VII}R^{VIII}$, $—OR^{VII}$, $—COR_{VII}$—$COOR_{VII}$—$CONR_{VII}R_{VII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ and $R^{III}$ independently are H, $C_{1-8}$heteroalkyl, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl; $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

L is Cl, Br, I, F, $OSO_2R^{IX}$, $O(CO)R^{IX}$ or $OCO_2R^{IX}$;

$R^{IX}$ is fluorinated $C_{1-8}$alkyl, $C_{1-8}$alkyl $C_{5-10}$aryl, $C_{5-10}$aryl$C_{1-8}$alkanyl, or $C_{5-10}$heteroaryl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

3. A method of synthesizing 2-substituted azole compounds of formula (I):

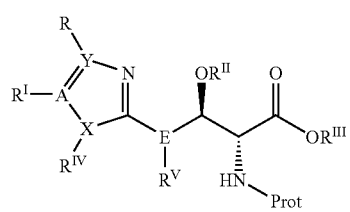

(I)

the method comprising (a) reacting an aldehyde of formula (II)

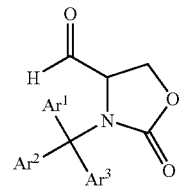

(II)

with an azole of formula (III)

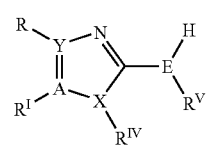

(III)

in the presence of a carbonylating agent of formula (IV)

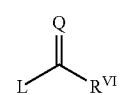

(IV)

to give an oxazolidone of formula (Ia)

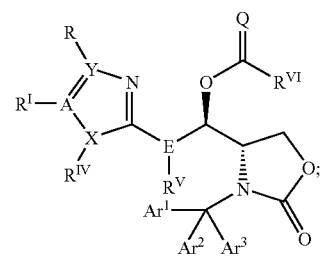

(Ia);

(b) reacting the oxazolidone of formula (Ia) so as to hydrolyze the triarylmethyl group, then reacting the resulting intermediate with Prot-Z wherein Prot-Z is an amino protecting agent selected from the group consisting of Prot-O-Prot, Prot-halide, Prot-N$_3$, $R^XO_2C$—$OCO_2N$=$C(C_6H_5)CN$, Prot-O-(1-benzotriazolyl), $R^XO_2C$—O—$C_6F_5$, $R^XO_2C$—O—$C6H_4$—$NO_2$, $R^XO_2C$—O—$CH(Cl)CCl_3$, $R^XO_2C$—O-2-pyridyl, $R^XO_2C$—S-2-pyridyl, $R^XO_2C$—S-Ph, $R^XO_2C$—OSu, $R^XO_2C$-(1-imidazoyl), $R^XO_2C$—CN, $R^XCO$—O—$C_6F_5$, $R^XCO$—CN, Fmoc-Cl, Fmoc-N$_3$, Fmoc-O-(1-benzotriazolyl), Fmoc-OSu, or Fmoc-O—$C_6F_5$, to give an azole-containing intermediate of formula (Ic)

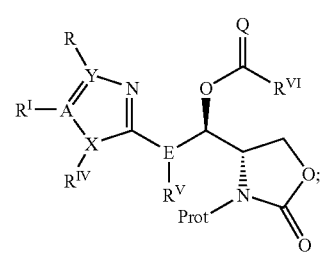

(Ic);

(c) reacting the intermediate of formula (Ic) so as to hydrolyze the O-(C=Q) bond, then reacting the intermediate with $R^{II}$-L to give an intermediate of formula (Id);

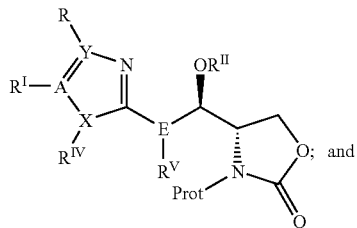

(Id);

(d) reacting the intermediate of formula (Id) so as to hydrolyze the oxazolidone group, then oxidizing the intermediate to give the 2-substituted azole of formula (I);

wherein $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy;

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ and $R^{III}$ independently are H, $C_{1-8}$heteroalkyl, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with L and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or —$NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Q is O or S;

L is Cl, Br, I, F, $OSO_2R^{IX}$, $O(CO)R^{IX}$ or $OCO_2R^{IX}$;

$R^{IX}$ is fluorinated $C_{1-8}$alkyl, $C_{1-8}$alkyl $C_{5-10}$aryl, $C_{5-10}$aryl$C_{1-8}$alkanyl, or $C_{5-10}$heteroaryl;

Prot is an amino protecting group selected from the group consisting of —$CO_2R^X$, —$COR^X$, and —$SO_2R^X$; and $R^X$ is $C_{1-8}$alkyl, $C_{1-5}$alkyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

4. The method of any of claims 1 to 3 wherein Prot is Boc, Fmoc, Alloc, Cbz, Ts, or Mtr.

5. The method of any of claims 1 to 3 wherein Prot is Boc or Fmoc.

6. The method of any of claims 1 to 3 wherein Prot is Boc.

7. The method of any of claims 1 to 3 wherein $Ar^1$, $Ar^2$, and $Ar^3$ are phenyl.

8. The method of any of claims 1 to 3 wherein X is N.

9. The method of any of claims 1 to 3 wherein A is C.

10. The method of any of claims 1 to 3 wherein Y is C.

11. The method of any of claims 1 to 3 wherein X is N, A is C, and Y is C.

12. The method of any of claims 1 to 3 wherein Q is S.

13. The method of any of claims 1 to 3 wherein E is a direct bond and RV is absent.

14. The method of any of claims 1 to 3 wherein R is H.

15. The method of any of claims 1 to 3 wherein RI is H.

16. The method of any of claims 1 to 3 wherein R and RI taken together are —(CH=CH)$_2$—.

17. The method of any of claims 1 to 3 wherein $R^{IV}$ is $C_{1-8}$alkyl $C_{5-10}$aryl$C_{1-8}$alkanyl or $C_{5-10}$aryl$C_{1-8}$heteroalkyl.

18. The method of any of claims 1 to 3 wherein $R^{IV}$ is methyl, Benzyl or —$CH_2OCH_2C_6H_5$.

19. The method of any of claims 1 to 3 wherein $R^V$ is absent, or H.

20. The method of any of claims 1 to 3 wherein $R^{IV}$ and $R^V$ together with E form a five to eight membered cyclic alkyl or cyclic heteroalkyl.

21. The method of any of claims 1 to 3 wherein $R^{IV}$ and $R^V$ together with E form a 6 membered cyclic alkanyl.

22. The method of any of claims 1 to 3 wherein $R^{VI}$ is $NMe_2$.

23. The method of any of claims 1 to 3 wherein $R^{VII}$ is $C_{1-8}$alkyl.

24. The method of any of claims 1 to 3 wherein $R^{VIII}$ is $C_{1-8}$alkyl.

25. The method of any of claims 1 to 3 wherein $R^{VII}$ and $R^{VIII}$ taken taken together form a three to seven membered cyclic alkanyl or cyclic heteroalkanyl.

26. The method of any of claims 1 to 3 wherein L is Cl, Br, $OSO_2R^{IX}$, or $O(CO)R^{IX}$.

27. The method of claim 26 wherein L is $OSO_2R^{IX}$, or $O(CO)R^{IX}$ and $R^{IX}$ is fluorinated $C_{1-8}$alkyl.

28. The method of any of claims 1 to 3 wherein L is Cl.

29. A 2-substituted azole compound of formula (I):

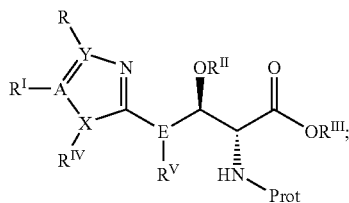

(I)

wherein

X is N or S;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

Y and A independently are C or N;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ and $R^{III}$ independently are H, $C_{1-8}$heteroalkyl, $C_{1-8}$alkyl, $C_{5-10}$aryl$C_{1-8}$alkanyl or $C_{1-8}$heteroalkyl;

Prot is an amino protecting group selected from the group consisting of —$CO_2R^X$, —$COR^X$, and —$SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

30. A compound of formula (Ia)

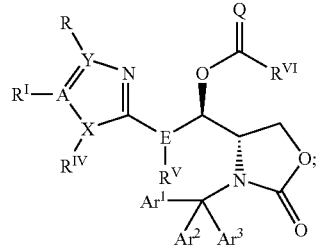

(Ia)

wherein

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —$NR^{VII}R^{VIII}$, —$OR^{VII}$, —$COR^{VII}$—$COOR^{VII}$—$CONR^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with L and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or —$NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Q is O or S; and $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy.

31. A compound of formula (Ib)

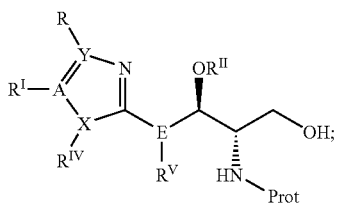

wherein

X is N;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryi$C_{1-8}$alkanyl, halogen, nitrile, —NR$^{VII}$R$^{VIII}$, —OR$^{VII}$, —COR$^{VII}$—COOR$^{VII}$—CONR$^{VII}$R$^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ is H, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Prot is an amino protecting group selected from the group consisting of —CO$_2$R$^X$, —COR$^X$, and —SO$_2$R$^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

32. A compound of formula (Ic)

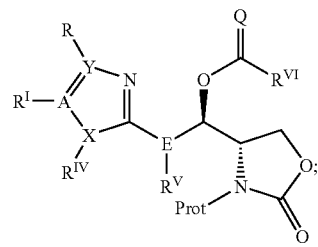

wherein

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, —NR$^{VII}$R$^{VIII}$, —OR$^{VII}$, —COR$^{VII}$—COOR$^{VII}$—CONR$^{VII}$R$^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VI}$ is $C_{1-8}$alkanyloxy or $-NR^{VII}R^{VIII}$;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Prot is an amino protecting group selected from the group consisting of $-CO_2R^X$, $-COR^X$, and $-SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

33. A compound of formula (Id)

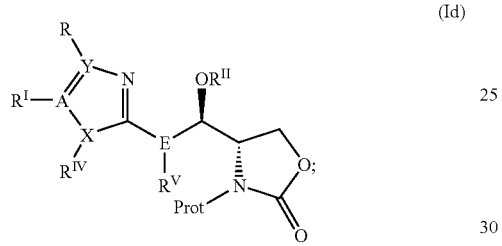

(Id)

wherein

X is N or S;

Y and A independently are C or N;

E is a direct bond or CH;

R and $R^I$ independently are H, $C_{1-8}$heteroalkyl, $C_{1-8}$alkyl, $C_{5-10}$aryl, heteroaryl, $C_{5-10}$aryl$C_{1-8}$alkanyl, $C_{1-8}$fluorinated alkyl, heteroaryl$C_{1-8}$alkanyl, halogen, nitrile, $-NR^{VII}R^{VIII}$, $-OR^{VII}$, $-COR^{VII}$—COOR$^{VII}$—CONR$^{VII}R^{VIII}$ or taken together form a five to eight membered carbocyclic or heterocyclic saturated or unsaturated ring, wherein the heteroaryl in any heteroaryl-containing R or $R^I$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{II}$ is H, $C_{1-8}$alkyl, $C_{5-10}$aryl$C_{1-8}$alkanyl or $C_{1-8}$heteroalkyl;

$R^{IV}$ is H, $C_{1-8}$alkyl, $C_{5-10}$aryl, heteroaryl, $C_{5-10}$aryl$C_{1-8}$alkanyl, $C_{5-10}$aryl$C_{1-8}$heteroalkyl, $C_{1-8}$heteroalkyl, or taken together with $R^V$ forms a five to eight membered cyclic alkanyl or cyclic heteroalkanyl, wherein the heteroaryl in any heteroaryl-containing $R^{IV}$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^V$ is absent when E is a direct bond, H, $C_{1-8}$alkyl, $C_{5-10}$aryl, $C_{5-10}$aryl$C_{1-8}$alkanyl, heteroaryl, or taken together with E and $R^{IV}$ forms a five to eight membered cyclic alkyl or cyclic heteroalkyl, wherein the heteroaryl in any heteroaryl-containing $R^V$ is independently selected from the group consisting of chromenyl, cinnolinyl, furanyl, imidazolyl, indazolyl, indolyl, indolizinyl, isobenzofuranyl, isochromenyl, isoindolyl, isoquinolinyl, isothiazolyl, isoxazolyl, naphthyridinyl, oxadiazolyl, oxazolyl, perimidinyl, phthalazinyl, pteridinyl, purinyl, pyranyl, pyrazinyl, pyrazolyl, pyridazinyl, pyridinyl, pyrimidinyl, pyrrolyl, pyrrolizinyl, quinazolinyl, quinolinyl, quinolizinyl, quinoxalinyl, tetrazolyl, thiadiazolyl, thiazolyl, thiophenyl, triazinyl, and triazolyl;

$R^{VII}$ and $R^{VIII}$ independently are $C_{1-8}$alkyl, $C_{5-10}$aryl, $C_{5-10}$aryl$C_{1-8}$alkanyl or taken taken together form a three to seven membered cyclic alkanyl or cyclic heteroalkanyl;

Prot is an amino protecting group selected from the group consisting of $-CO_2R^X$, $-COR^X$, and $-SO_2R^X$; and $R^X$ is $C_{1-8}$alkyl, $C_{1-5}$alkanyl substituted with 1-11 chlorine atoms, $C_{5-10}$aryl, $C_{5-10}$aryl$C_{1-8}$alkanyl, $C_{3-8}$heteroalkanyl, $C_{5-10}$heteroaryl, or Fmoc.

34. A compound of formula (II)

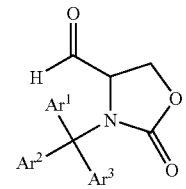

(II)

wherein $Ar^1$, $Ar^2$ and $Ar^3$ independently are phenyl or phenyl optionally substituted with halogen, $C_{1-8}$alkyl, $C_{1-8}$alkyloxy, nitro, $C_{1-8}$alkylamino, nitrile, or benzoyloxy.

35. The compound of any of claims 29 to 33 wherein Prot is Boc, Fmoc, Alloc, Cbz, Ts, or Mtr.

36. The compound of any of claims 29 and 31 to 33 wherein Prot is Boc or Cbz.

37. The compound of any of claims 29 and 31 to 33 wherein Prot is Boc.

38. The compound of any of claims 30 and 34 wherein $Ar^1$, $Ar^2$, and $Ar^3$ are phenyl.

39. The compound of any of claims 29, 30, 32, 33 wherein X is N.

40. The compound of any of claims 29 to 33 wherein A is C.

41. The compound of any of claims 29 to 33 wherein Y is C.

42. The compound of any of claims 29 to 33 wherein X is N, A is C, and Y is C.

43. The compound of any of claims 30 or 32 wherein Q is S.

44. The compound of any of claims 29 to 33 wherein E is a direct bond and $R^V$ is absent.

45. The compound of any of claims 29 to 33 wherein R is H.

46. The compound of any of claims 29 to 33 wherein $R^I$ is H.

47. The compound of any of claims 29 to 33 wherein R and $R^I$ taken together are —(CH=CH)$_2$—.

48. The compound of any of claims 29 to 33 wherein $R^{IV}$ is C$_{1-8}$alkyl C$_{5-10}$arylC$_{1-8}$alkanyl or C$_{5-10}$arylC$_{1-8}$heteroalkyl.

49. The compound of any of claims 29 to 33 wherein $R^{IV}$ is methyl, Benzyl or —CH$_2$OCH$_2$C$_6$H$_5$.

50. The compound of any of claims 29 to 33 wherein $R^V$ is absent, or H.

51. The compound of any of claims 29 to 33 wherein $R^{IV}$ and $R^V$ together with E form a five to eight membered cyclic alkyl or cyclic heteroalkyl.

52. The compound of any of claims 29 to 33 wherein $R^{IV}$ and $R^V$ together with E form a 6 membered cyclic alkanyl.

53. The compound of any of claims 30 or 32 wherein $R^{VI}$ is NMe$_2$.

54. The compound of any of claims 29 to 33 wherein $R^{VII}$ is C$_{1-8}$alkyl.

55. The compound of any of claims 29 to 33 wherein $R^{VIII}$ is C$_{1-8}$alkyl.

56. The compound of any of claims 29 to 33 wherein $R^{VII}$ and $R^{VIII}$ taken taken together form a three to seven membered cyclic alkanyl or cyclic heteroalkyl.

* * * * *